US012408971B2

(12) United States Patent
Ullrich et al.

(10) Patent No.: US 12,408,971 B2
(45) Date of Patent: Sep. 9, 2025

(54) ELECTROSURGICAL RESECTOR TOOL

(71) Applicant: CREO MEDICAL LIMITED, Gwent (GB)

(72) Inventors: George Christian Ullrich, Anglesey (GB); Christopher Paul Hancock, Chepstow (GB); Louis Turner, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 0 days.

(21) Appl. No.: 18/703,683

(22) PCT Filed: Nov. 10, 2022

(86) PCT No.: PCT/EP2022/081501
§ 371 (c)(1),
(2) Date: Apr. 22, 2024

(87) PCT Pub. No.: WO2023/104424
PCT Pub. Date: Jun. 15, 2023

(65) Prior Publication Data
US 2024/0325072 A1     Oct. 3, 2024

(30) Foreign Application Priority Data
Dec. 10, 2021   (GB) ...................................... 2117879

(51) Int. Cl.
*A61B 18/14*         (2006.01)
*A61B 18/18*         (2006.01)
*A61B 18/00*         (2006.01)

(52) U.S. Cl.
CPC ...... *A61B 18/1445* (2013.01); *A61B 18/1815* (2013.01); *A61B 2018/00601* (2013.01); *A61B 2018/0063* (2013.01); *A61B 2018/146* (2013.01)

(58) Field of Classification Search
CPC ............ A61B 18/1445; A61B 18/1815; A61B 18/085; A61B 18/1442; A61B 18/18;
(Continued)

(56) References Cited

U.S. PATENT DOCUMENTS 5,819,738 A * 10/1998 Slater ..................... A61B 10/06
606/205
2011/0184404 A1 * 7/2011 Walberg ............. A61B 18/1445
606/41

(Continued)

FOREIGN PATENT DOCUMENTS

EP        2359762 A2    8/2011
EP        3841993 A1    6/2021
(Continued)

OTHER PUBLICATIONS

International Preliminary Report on Patentability, issued by the International Searching Authority in Corresponding International Patent Application No. PCT/EP2022/081501, dated Jul. 18, 2023.
(Continued)

*Primary Examiner* — Thomas A Giuliani
(74) *Attorney, Agent, or Firm* — ArentFox Schiff LLP

(57) ABSTRACT

An electrosurgical resector tool comprising: an energy conveying structure for carrying radiofrequency electromagnetic energy and/or microwave electromagnetic energy; a tool tip mounted at a distal end of the energy conveying structure, wherein the tool tip comprises a first jaw and a second jaw. The first jaw comprises a first pair of electrodes that are electrically isolated. The first pair of electrodes is coupled to the energy conveying structure. The first and second jaw are movable relative to each other between a closed position in which the first and second jaw lie alongside each other, and an open position in which the second jaw is spaced from the first jaw for receiving biological tissue. The first jaw extends in a distal direction beyond the
(Continued)

second jaw in the closed position. The first jaw includes a distal end face, the first pair of electrodes being exposed on the distal end face.

11 Claims, 12 Drawing Sheets

(58) Field of Classification Search
CPC .... A61B 2018/146; A61B 2018/00607; A61B 2018/00601; A61B 2018/0063; A61B 2018/126
USPC ............. 606/33, 48, 50–52; 607/99, 101
See application file for complete search history.

(56) References Cited

U.S. PATENT DOCUMENTS

| | | | |
|---|---|---|---|
| 2015/0080889 A1* | 3/2015 | Cunningham | A61B 18/1445 606/42 |
| 2016/0331455 A1* | 11/2016 | Hancock | A61B 18/1815 |

FOREIGN PATENT DOCUMENTS

| WO | WO 2017/189413 A1 | 11/2017 |
|---|---|---|
| WO | WO 2020/256053 A1 | 12/2020 |
| WO | WO 2021/105131 A1 | 6/2021 |
| WO | WO 2022/100934 A1 | 5/2022 |
| WO | WO 2022/128230 A1 | 6/2022 |

OTHER PUBLICATIONS

International Search Report and Written Opinion, issued by the International Searching Authority in corresponding International Patent Application No. PCT/EP2022/081501, dated Feb. 22, 2023.
Search Report Under Section 17, issued by the United Kingdom Intellectual Property Office in corresponding United Kingdom Application No. GB2117879.3, dated Apr. 28, 2022.

* cited by examiner

ELECTROSURGICAL RESECTOR TOOL

CROSS-REFERENCE TO RELATED APPLICATIONS

This application is a National Stage Entry of International Application No. PCT/EP2022/081501, filed Nov. 10, 2022, which claims priority to United Kingdom Patent Application No. 2117879.3, filed Dec. 10, 2021. The disclosures of the priority applications are hereby incorporated in their entirety by reference.

FIELD OF THE INVENTION

The invention relates to an electrosurgical resector tool and an electrosurgical apparatus for cutting, coagulating, and ablating biological tissue. In particular, the invention relates to an electrosurgical resector tool and an electrosurgical apparatus capable of delivering radiofrequency (RF) energy and/or microwave frequency energy for cutting biological tissue, haemostasis (i.e. sealing broken blood vessels by promoting coagulation of blood), and tissue/or ablation.

BACKGROUND

Surgical resection is a means of removing sections of organs from within the human or animal body. The organs may be highly vascular. When tissue is cut (i.e. divided or transected), small blood vessels may be damaged or ruptured. Initial bleeding is followed by a coagulation cascade where the blood is turned into a clot in an attempt to plug the bleed. During an operation it is desirable for a patient to lose as little blood as possible, so various devices have been developed in an attempt to provide bleeding-free cutting. For endoscopic procedures, it is also undesirable for a bleed to occur and not to be dealt with expediently, since the flow of blood may obscure the operator's vision.

Instead of a sharp blade, it is known to use RF energy to cut biological tissue. The method of cutting using RF energy operates using the principle that as an electric current passes through a tissue matrix (aided by the ionic cell contents), the impedance to electron flow across the tissue generates heat. When a pure sine wave is applied to the tissue matrix, enough heat is generated within the cells to vaporize the water content of the tissue. There is thus a huge rise in the internal cell pressure that cannot be controlled by the cell membrane, resulting in rupture of the cell. When this occurs over a large area, it can be seen that the tissue is transected. The above procedure works elegantly in lean tissue, but it is less efficient in fatty tissue because there are fewer ionic constituents to aid the passage of electrons. This means that the energy required to vaporize the contents of the cells is much greater, since the latent heat of vaporization of fat is much greater than the latent heat of vaporization of water.

RF coagulation operates by applying a less efficient waveform to the tissue, whereby instead of being vaporized, the cell contents are heated to around 65° C., drying out the tissue by desiccation and denaturing the proteins in the vessel walls. This denaturing acts as a stimulus to the coagulation cascade, so clotting is enhanced. At the same time the collagen in the wall is denatured, turning from a rod-shaped to a coil-shaped molecule, causing the vessel to contract and reduce in size, giving the clot an anchor point, and a smaller area to be plugged. However, RF coagulation is less efficient when fatty tissue is present because the electrical effect is diminished. It can thus be very difficult to seal fatty bleeders. Instead of having clean white margins, the tissue has a blackened burned appearance.

Tissue ablation using microwave electromagnetic (EM) energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating. This principle is harnessed in microwave ablation therapies, where water molecules in target tissue are rapidly heated by application of a localised electromagnetic field at microwave frequencies, resulting in tissue coagulation and cell death.

SUMMARY OF THE INVENTION

At its most general the present invention provides an electrosurgical resector tool (or electrosurgical resector instrument) having an energy delivery structure that provides a plurality of operational modalities that facilitate biological tissue cutting and sealing using radiofrequency (RF) electromagnetic energy and/or microwave EM energy. In particular, the invention relates to combined actuation and energy delivery mechanisms that are compact enough to enable the tool to be insertable through an instrument channel of a surgical scoping device, such as an endoscope, gastroscope or bronchoscope. The device could also be used to perform laparoscopic or open surgery, i.e. the bloodless resection of a liver lobe with the abdominal cavity open.

The invention represents a development to the electrosurgical resector tool concept discussed in GB2567480. The electrosurgical resector tool of the invention comprises a pair of jaws, wherein a first jaw comprises a first pair of electrodes and a second jaw optionally comprises a single electrode (i.e. only one electrode is present on the second jaw) or second pair of electrodes (i.e. two electrodes are present on the second jaw). This allows the electrosurgical resector tool to be operated according to three complimentary modalities: (i) a gliding RF-based cut when the jaws are closed, (ii) a scissor-type cut performed on tissue grasped between the jaws using a combination of RF energy and applied pressure, and (iii) a coagulation or vessel sealing operating performed on tissue grasped between the jaws using a combination of microwave energy and applied pressure. The inventors having found that, by providing two, three, or four electrodes on a resector tool as described herein, it is possible to improve the tool's ability to cut and coagulate tissue using EM energy. In particular, such an arrangement of electrodes may enable multiple RF fields to be established across the jaws, which may result in a smoother, more uniform cut. Similarly, such an electrode configuration may lead to more effective tissue coagulation and ablation using microwave energy, by enabling a more uniform microwave field to be emitted. For the avoidance of doubt, by "single electrode" it should be understood that the second jaw comprises only one electrode, and no other electrodes for delivering RF and/or microwave energy are provided on the second jaw.

There is provided an electrosurgical resector tool comprising: an energy conveying structure for carrying radiofrequency electromagnetic energy and/or microwave electromagnetic energy; a tool tip (or instrument tip or tip of the scoping device) mounted at a distal end of the energy conveying structure, wherein the tool tip comprises a first jaw and a second jaw; wherein the first jaw comprises a first pair of electrodes that are electrically isolated from one another; wherein the first pair of electrodes is coupled to the energy conveying structure, wherein the first jaw and the second jaw are movable relative to each other between a closed position in which the first jaw and the second jaw lie alongside each other, and an open position in which the second jaw is spaced from the first jaw by a gap for receiving biological tissue; wherein the first jaw extends in a distal direction beyond the second jaw in the closed position; and wherein the first jaw includes a distal end face, the first pair of electrodes being exposed on the distal end face.

The electrosurgical resector tool can be considered an electrosurgical instrument (such as an electrosurgical resector instrument) and/or an electrosurgical (scoping) device (having resecting functionalities). The electrosurgical resector tool can be configured to (uniformly) radiate microwave radiation for sealing (blood) vessels. The electrosurgical resector tool additionally provides a cutting or resecting function at the distal end face as the first pair of electrodes is exposed at the distal end face. Thus, electric current can flow between the pair of electrodes at the distal end face. The electrosurgical resector tool not only provides cutting between the jaws but also at the distal end face. As the first jaw extends beyond the second jaw in the closed position, the distal end face is the most distal surface of the electrosurgical resector tool. This means, when the electrosurgical resector tool is moved or pushed in the distal direction, the distal end face firstly comes in contact with a tissue (in the closed position). The electrosurgical resector tool has a small outer diameter such that the distal end face also has a small area; the outer diameter of the electrosurgical resector tool is smaller than a cavity of a scoping device or endoscope through which the electrosurgical resector tool can be moved. This allows precise cutting at the distal end face. In particular, the electrosurgical resector tool can cut its way through issue, for example to gain access to a cavity.

The energy conveying structure may comprise a coaxial transmission line having an inner conductor separated from an outer conductor by a dielectric material. The first pair of electrodes may be coupled to the energy conveying structure, such that the first pair of electrodes is operable as active and return electrodes for delivering radiofrequency electromagnetic energy carried by the energy conveying structure. Optionally, the tool tip is operable as a microwave field emitting structure for emitting microwave electromagnetic energy carried by the energy conveying structure.

The energy conveying structure may be disposed in a lumen of a shaft (or outer sheath), such that the tool tip protrudes from a distal end of the shaft. The shaft may be any suitable shaft through which the coaxial transmission line can be inserted. The shaft may be flexible, e.g. suitable for bending or other steering to reach the treatment site. A flexible shaft may enable the device to be usable in a surgical scoping device such as an endoscope. In other examples, the shaft may be rigid, e.g. for use in open surgery or with a laparoscope.

The coaxial transmission line may be adapted to convey both the RF EM energy and the microwave EM energy. Alternatively, the energy conveying structure may comprise different routes for the RF EM energy and microwave EM energy. For example, the microwave EM energy may be delivered through the coaxial transmission line, whereas the RF EM energy can be delivered via twisted pair wires or the like. The coaxial transmission line may be in the form of a flexible coaxial cable.

The first jaw and the second jaw are mounted at the distal end of the energy conveying structure such that they are movable relative to one another between the open and closed positions. Various types of relative movement between the jaws may be used. The relative movement between the first jaw and the second jaw may comprise rotational and/or translational movement. At least one of the first jaw and the second jaw may be movably mounted relative to the distal end of the energy conveying structure, to enable relative movement between the first and second jaws. In some cases, only one of the first and second jaws may be movably mounted relative to the distal end of the energy conveying structure, whilst in other cases both the first and second jaws may be movably mounted relative to the distal end of the energy conveying structure.

As an example, the first jaw and second jaw may be pivotable relative to one another, e.g. such that an opening angle between the first jaw and the second jaw can be adjusted. This example may resemble a scissor-type closure. The first jaw and/or the second jaw may be pivotably mounted at the distal end of the energy conveying structure.

In another example, it may be beneficial for the gap between the first and second jaws to be uniform once tissue is grasped therebetween, e.g. to ensure that the energy supplied is uniform along the length of the jaws. In this example, the first jaw and the second jaw may be configured to remain parallel when they are moved relative to one another. For instance, the first jaw and the second jaw may be parallel when the jaws are in the open position, and the first and second jaws may remain parallel when sliding past one another to the closed position.

The first jaw and the second jaw can be moved between the open position and the closed position. The open position is the position in which the first jaw and the second jaw are furthest away from each other. The closed position is the position which the first jaw and the second jaw are closest to each other or overlap with each other. There is a plurality of intermediate positions between the open position and the closed position. The first jaw and the second jaw can be continuously positioned between the open position and the closed position or there are a number of discrete intermediate positions between the open position and the closed position.

The first jaw may comprise a first blade element, and/or the second jaw may comprise a second blade element. Then, when the jaws are in the closed position, the first blade element may lie alongside the second blade element, and when the jaws are in the open position, there may be a gap between the first blade element and the second blade element for receiving biological tissue.

The first blade element and the second blade element may be configured to cut tissue disposed in the gap between the first and second jaws when the first and second jaws are moved from the open position to the closed position. Thus, the first blade element and the second blade element may each include a cutting (e.g. sharp) edge that is arranged for cutting tissue. A cutting interface may be defined between the first jaw and the second jaw, corresponding to a region in which tissue between the jaws is cut when the jaws are closed.

The first blade element and the second blade element may be arranged to slide past one another when the first and second jaws are moved between the open position and closed position, e.g. to effect mechanical cutting of tissue through application of a shearing force. Thus, cutting effected by the first and second blade elements may resemble a scissors-type cutting mechanism.

In the closed position, both the first jaw and the second jaw are orientated parallel to the distal direction. In other words, in the closed position, the first jaw is positioned parallel to the second jaw. In the open position, one of the first jaw and the second jaw, optionally the static or non-movable jaw, remains positioned parallel to the distal direction. The distal direction can be parallel to the longitudinal direction of the electrosurgical resector tool. In the closed position, the first jaw can be longer in the distal direction than the second jaw—the first jaw protrudes from the second jaw in the distal direction.

The first and/or second blade element may include one or more serrations (e.g. teeth). The serrations may facilitate gripping and cutting tissue located in the gap between the jaws.

The electrosurgical resector tool may comprise an actuator for controlling movement of the second jaw relative to the first jaw. The actuator may comprise any suitable type of actuator for controlling relative movement between the jaws. As an example, the actuator may comprise a control rod that extends along the energy conveying structure (e.g. inside the shaft), and that is movable along its length to control the position of one or both of the jaws. The control rod may have an attachment feature engaged with one or both of the first and second jaws, whereby longitudinal movement of the control rod causes movement of the second jaw relative to the first jaw. The attachment feature may be a hook or any suitable engagement for transmitting push and pull forces to the one or both of the jaws.

The first pair of electrodes is disposed on the first jaw, with a first electrode in the first pair acting as an active electrode for the RF EM energy, and a second electrode in the first pair acting as a return electrode for the RF EM energy. In this manner, RF EM energy carried by the energy conveying structure can be delivered to tissue via the first pair of electrodes. The first pair of electrodes can establish a first RF cutting field with the RF EM energy from the energy conveying structure, in order to cut target tissue. The first pair of electrodes may be exposed on a surface of the first jaw, so that they can contact target tissue to deliver RF EM energy into the target tissue. In particular, the first pair of electrodes can contact target issue to deliver RF EM energy into the target tissue at the distal end face.

The single electrode or the second pair of electrodes are disposed on the second jaw and may act as either an active electrode and/or a return electrode for RF EM energy. In particular, the single electrode is operable as an active electrode when the inner electrode of the first jaw is operable as a return electrode, or is operable as a return electrode when the inner electrode of the first jaw is operable as an active electrode. In this way, the single electrode may cooperate with the first pair of electrodes on the first jaw to establish a second RF cutting field with the RF EM energy from the energy conveying structure, in order to cut target tissue. The single electrode on the second jaw may be exposed on a surface of the second jaw, so that it can contact target tissue to deliver RF EM energy into the target tissue.

Thus, when RF EM energy is conveyed by the energy conveying structure, a first RF cutting field is established by the first pair of electrodes, and a second RF cutting field is established between jaws by the single electrode or one of the second pair of electrodes on the second jaw and the first pair of electrodes. Thus, RF cutting may occur at the first jaw and also between the two jaws. This may enable RF cutting to be performed across a larger region of tissue, as well as enable more uniform RF cutting to be performed.

Moreover, the three electrodes serve to define a microwave field emitting structure for emitting (or radiating) microwave EM energy from the energy conveying structure. Thus, microwave EM energy carried by the energy conveying structure may be radiated from the electrodes into target tissue, in order to coagulate and/or ablate the target tissue. The specific shape of the microwave field(s) emitted will depend on the arrangement of electrodes in the jaws. For example, electrodes in both jaws may together form a microwave field emitting structure, such that a common microwave field is emitted across both jaws. Using paired electrodes to radiate microwave EM energy may serve to improve a uniformity and symmetry of the emitted microwave field across the jaws, which may improve an effectiveness of treatment of tissue with microwave EM energy.

In an optional embodiment, the first jaw comprises a first planar dielectric element having an inner surface that faces towards the second jaw and an outer surface that faces away from the second jaw, the first pair of electrodes comprising an inner electrode and an outer electrode, the inner electrode being arranged on the inner surface of the first planar dielectric element and the outer electrode being arranged on the outer surface of the first planar dielectric element. The second jaw may comprise a second planar dielectric element having an inner surface that faces towards the first jaw in the closed position and an outer surface that faces away from the first jaw in the closed position. The second jaw may comprise an inner electrode arranged on the inner surface of the second planar dielectric element, and/or an outer electrode arranged on the outer surface of the second planar dielectric element.

The electrodes may thereby be substantially aligned with one another in a lateral direction when the jaws are closed. This may enable effective treatment of target tissue over a large area when the jaws are closed. Further, as the first jaw is longer than the second jaw, this configuration allows to cut/resect tissue at the distal end face using the first pair of electrodes.

The first planar dielectric element and the second planar dielectric element may be substantially parallel to one another, e.g. a plane defined by the inner surface of the first planar dielectric element may be substantially parallel to a plane defined by the inner surface of the second planar dielectric element. The first planar dielectric element and the second planar dielectric element may each be aligned parallel to a plane in which the first jaw and second jaw are movable relative to one another.

Each of the first and second planar dielectric elements may be formed by a piece of dielectric (i.e. insulating) material, such as from ceramic (e.g. alumina). Herein, reference to "planar" element may mean a flat piece of material having a thickness that is substantially less that its width and length. Each planar dielectric element may have a length dimension aligned in a longitudinal direction, a thickness dimension aligned in a lateral direction, and a width dimension orthogonal to both the length and thickness dimensions. A plane of a planar dielectric element is a plane in which the length and width dimensions lie, i.e. a plane orthogonal to the width dimension. The inner surface and outer surfaces of each planar dielectric element may be parallel to the plane of the planar dielectric element, i.e. they may be orthogonal to the width dimension. The inner and outer surfaces of each planar dielectric element may be arranged on opposite sides of the planar dielectric element, with respect to its width.

The distal end face may be a surface of the first jaw that is visible when viewed along the longitudinal direction on the first jaw.

Using a planar dielectric element in each jaw, on which the electrodes are arranged, may greatly facilitate fabrication of the tool tip. This is because the electrodes can easily be formed on their inner and/or outer surfaces, e.g. by depositing conductive material onto the surfaces and/or by attaching conductive elements to the surfaces. In contrast, in prior art resector tools, the jaws are typically made of a conductive material which is coated with an insulating material, with electrodes being defined by an area of the jaws where the insulating material is etched away. Defining electrodes by etching away insulating material may be a tedious and time-consuming process. Additionally, it was found that tissue may stick to the insulating material, rendering the tool tip difficult to clean. Thus, using the planar dielectric elements in the jaws may facilitate manufacture of the tool tip, as well as avoid tissue sticking to the tool tip.

In some cases, the first planar dielectric element may define the first blade element. For example the first planar dielectric element may comprise a cutting edge that is configured to contact tissue located between the jaws and to cut the tissue when the jaws are closed. Then, the inner electrode of the first pair of electrodes may be formed at or near the cutting edge of the first planar dielectric element.

Similarly, the second planar dielectric element may define the second blade element, e.g. the second planar dielectric element may comprise a cutting edge this is configured to contact and cut tissue located between the jaws. Then, where the single electrode is an inner electrode or the inner electrode of the second pair of electrodes, the inner electrode of the second pair may be formed at or near the cutting edge of the second planar dielectric element.

Where the first planar dielectric element defines the first blade element and the second planar dielectric element defines the second blade element, the inner surface of the first planar dielectric element may be arranged to slide across the inner surface of the second planar dielectric element when the jaws are moved between the open and closed positions.

In an optional embodiment, the inner electrode of the first pair of electrodes on the first jaw may comprise a first conductive layer formed on the inner surface of the first planar dielectric element; the outer electrode of the first jaw comprises a second conductive layer formed on the outer surface of the first planar dielectric element; the inner electrode of the second jaw comprises a first conductive layer formed on the inner surface of the second planar dielectric element; and/or the outer electrode of the second jaw comprises a second conductive layer formed on the outer surface of the second planar dielectric element.

Thus, each inner electrode may be formed by a respective layer of conductive material directly on the inner surface of the respective planar dielectric element and/or each outer electrode may be formed by a respective layer of conductive material directly on the outer surface of the respective planar dielectric element. For example, the layer of conductive material may be deposited using any suitable deposition technique, or the layer of conductive material may be otherwise mounted to the inner and/or outer surface (e.g. via an adhesive). The conductive layer for each inner electrode may be formed of any suitable conductive material, such as gold. The single electrode of the second jaw may be formed on the inner or outer surface of the second planar dielectric element, such that the single electrode is an inner or outer electrode.

The first conductive layer of the first and/or the second jaw may extend in the longitudinal direction, i.e. it may extend along all or part of a length of first and/or second planar dielectric element. Likewise, the second conductive layer of the first and/or the second jaw may extend in the longitudinal direction, i.e. it may extend along all or part of a length of the first and/or second planar dielectric element.

Preferably, the first jaw may comprise a third planar dielectric element having an inner surface that faces towards the second jaw, the third planar dielectric element being arranged on an inner surface of the inner electrode of the first jaw. Additionally or alternatively, the second jaw may comprise a fourth planar dielectric element having an inner surface that faces towards the first jaw, the fourth planar dielectric element being arranged on an inner surface of the single electrode of the second jaw. For example, the third and/or fourth planar dielectric element may be applied as a dielectric coating which provides an insulating barrier between the inner electrodes. For example, the coating could be a ceramic (e.g. alumina) coating, diamond-like coating, enamel coating or silicon-based paint coating. This coating may be further coated with Parylene N to seal the insulating coating (e.g. coated with a layer between 2 and 10 micrometres deep) which penetrates the pores and makes the insulator waterproof. Alternatively, the dielectric coating may be a thermoplastic polymer, e.g. polyether either ketone (PEEK) or the like. The dielectric coating may ensure that the inner electrode is exposed substantially only at an upper surface of the blade element, which may ensure that EM energy is focused into the desired region. By providing a third and/or fourth dielectric element in this way, it can be ensured that there is a minimal risk of electrical breakdown or discharge between the two inner electrodes, such that energy is preferentially directed into tissue. Such an arrangement may also improve symmetry between the jaws, which may in turn improve a symmetry of the RF and microwave energy emitted by the tool tip.

Furthermore, in some cases, the outer electrode of the first and/or second pair of electrodes may comprise a third conductive layer formed on the outer surface of the first planar dielectric element. The third conductive layer may be formed in a similar manner to the first and second conductive layers mentioned above. Of course, in some examples, the single electrode of the second jaw may be formed in a similar manner.

Thus, no patterning and etching of an insulating layer on either of the jaws may be required in order to form the electrodes, which may greatly facilitate manufacture of the tool tip.

The first pair of electrodes may be flush with a front side of the first planar dielectric element such that the first pair of electrodes contacts tissue if the tissue is in contact with the front side of the first planar dielectric element. Similarly, the inner electrode and/or the outer electrode of the second pair of electrodes may be flush with a front side of the second planar dielectric element such that the inner electrode and/or the outer electrode of the second pair of electrodes contacts tissue if the tissue is in contact with the front side of the second planar dielectric element.

The first jaw may further comprise a first cover which can be a first conductive shell. The first cover may be attached to the outer surface of the first planar dielectric element. The outer or second conductive layer of the first pair of electrodes may be arranged between the first cover and the first planar dielectric element. The first cover may be in electrical contact with the second conductive layer and, thus, arranged to form at least part of the outer electrode of the first pair of electrodes. Thus, the outer electrode may comprise a conductive shell (the first cover) mounted on the outer surface of the corresponding planar dielectric element. The first cover or the first conductive shell may define an outer surface of the first jaw.

In some embodiments, the second jaw may similarly comprise a second cover which can be a second conductive shell. The second cover is attached to the outer surface of the second planar dielectric element. The outer or second conductive layer of the second pair of electrodes may be arranged between the second cover and the second planar dielectric element. The second cover may be in electrical contact with the outer or second conductive layer and, thus, arranged to form at least part of the outer electrode of the second jaw.

The first and/or second covers may thus serve the dual purposes of defining a part of the outer electrode, as well as protecting the planar dielectric element to which it is mounted. The first and/or second covers may be formed of a piece of conductive material which is attached to the outer surface of the corresponding planar dielectric element (e.g. via an adhesive and/or a mechanical fastening). Any suitable conductive material may be used for the conductive shell, such as stainless steel.

A surface area of the first and/or second cover may be larger than a surface area of the inner (first) and/or outer (second) conductive layers of the first and second pairs of electrodes. For instance, a first and/or second cover may be formed of a relatively thick block of conductive material that covers all or most of the outer surface of a planar dielectric element, whilst the inner (first) and/or outer (second) conductive layers may be formed as a relatively thin and/or narrow conductive layer on the inner and/or outer surface of the first and/or second planar dielectric element. Thus, the first and/or second cover may serve to increase a surface area of the outer electrode relative to an inner electrode.

The inventors have found that, when a pair of spaced electrodes having different sizes are used to perform RF cutting of tissue, the tissue tends to be cut in the vicinity the smaller of the two electrodes. Accordingly, using a conductive shell (first and/or second cover) with a large surface area compared to the inner electrode may ensure that RF cutting of tissue occurs near the inner electrode. This may enable a well-defined cut to be made in tissue located between the jaws using RF EM energy. In particular, this may serve to ensure that the cut produced by the RF EM energy is located at or near the cutting interface between the blade elements.

Advantageously, the outer electrode of the first jaw and the outer electrode of the second jaw (which can be the single electrode of the second jaw) may be electrically coupled to one another. This may help provide symmetry of the RF and/or microwave EM fields emitted by the tip, in particular being symmetrical about the inner electrode of the first jaw and the region between the first jaw and the second jaw. For example, the outer electrode of the first jaw and the outer electrode of the second jaw may both be coupled to a common conductor in the energy conveying structure, such that they are electrically coupled via the energy conveying structure. In addition, the inner electrode of the first jaw and the inner electrode of the second jaw may both be coupled to a common conductor in the energy conveying structure, such that they are electrically coupled via the energy conveying structure.

The tool tip may further comprise a base structure that connects the outer electrode of the first jaw and the outer electrode of the second jaw to the distal end of the energy conveying structure. For example, the base structure may include a first base part that rigidly connects the outer electrode of the first jaw to the distal end of the energy conveying structure, and a second base part to which the second jaw is pivotably connected, such that the second jaw is pivotable relative to the second base part.

The base structure may be any suitable structure for supporting the jaws at the end of the energy conveying structure. The base structure may, for example comprise an arm which is secured to the distal end of the energy conveying structure at one end, and connected to the first and second jaws at another end. Such a base structure may serve to reinforce the distal end of the energy conveying structure (which may typically be flexible), and facilitate transmitting longitudinal forces to the tool tip. The base structure may comprise a rigid material (e.g. a metal, such as stainless steel).

The first jaw and/or the second jaw may be movably connected to the base structure, to enable relative movement between the first and second jaws. For example, the first jaw and/or the second jaw may be pivotably connected to the base structure.

In some cases, the first base part may be a part of the first cover, i.e. the first cover may form part of the base structure. For instance, the first base part may be a part of the first cover that extends between the first jaw and the distal end of the energy conveying structure. This may serve to ensure a rigid connection between the first jaw and the distal end of the energy conveying structure, as well as facilitate electrical connection between the outer electrode in the first pair and the energy conveying structure.

The base structure may comprise (e.g. be made of) an electrically conductive material that electrically connects the first cover to a first one of the inner conductor and the outer conductor at a distal end of the coaxial transmission line. In this manner, the first cover may be directly connected to a conductor of the coaxial transmission line via the base structure. For example, the first base part may comprise an electrically conductive material that electrically connects the first conductive shell to the first one of the inner conductor and the outer conductor.

Additionally or alternatively, the base structure may comprise (e.g. be made of) an electrically conductive material that electrically connects the inner or outer electrode of the second jaw to the first one of the inner conductor and the outer conductor at a distal end of the coaxial transmission line. In this manner, the inner electrode of the second jaw may be directly connected to a conductor of the coaxial transmission line via the base structure. For example, the second base part may comprise an electrically conductive material that electrically connects the inner electrode of the second jaw to the first one of the inner conductor and the outer conductor.

Where the first cover and the outer electrode of the second jaw are electrically coupled to one another, the base structure may comprise (e.g. be made of) an electrically conductive material that connects each of the first and second covers to a first one of the inner conductor and the outer conductor at a distal end of the coaxial transmission line. Thus, the first conductive shell and the inner electrode of the second jaw may be electrically coupled via the base structure.

The base structure may define a cavity in which the inner electrodes of the first and/or second jaws are electrically connected to a second one of the inner conductor and the outer conductor at the distal end of the coaxial transmission line. In this manner, the base structure may serve to protect the electrical connection between the inner electrodes of the first and/or second jaws with the second one of the inner conductor and the outer conductor. The conductive material of the base structure may also serve to provide electromagnetic shielding for the electrical connection inside the cavity. The cavity may be a space or void defined within base structure.

The cavity may contain a dielectric material. This may ensure that the electrical connection in the cavity is electrically insulated, in order to avoid breakdown between the electrical connections inside the cavity and the surrounding base structure. The dielectric material may be any suitable type of dielectric material. As an example, an electrical potting material may be used as the dielectric material in the cavity, such as a thermosetting plastic, silicone, epoxy or resin.

The base structure may comprise an opening formed in a sidewall of the base structure for injecting a dielectric material into the cavity. For example, the opening may be a hole or aperture formed in the sidewall of the base structure. This may enable the dielectric material to be injected into the cavity, after assembly of the tool tip at the distal end of the energy conveying structure. This may facilitate assembly of the tool tip.

In some embodiments, the outer electrode of the first jaw and the outer electrode of the second jaw are both electrically connected to a first one of the inner conductor and the outer conductor, and the inner electrode of the first jaw is electrically connected to a second one of the inner conductor and the outer conductor. Such a configuration of electrodes may enable a first RF cutting field to be established between the pair of the electrodes on the first jaw, and a second RF cutting field to be established between the inner conductor of the first jaw and the inner conductor of the second jaw. The two RF fields may be substantially symmetrical about the cutting interface between the blade elements, which may yield a highly uniform cut of tissue held between the jaws. Additionally, with such an electrode configuration, a substantially symmetrical microwave field may be emitted across the jaws, enabling microwave ablation and/or coagulation of tissue around the jaws.

Advantageously, the first pair of electrodes and the single electrode may be operable together as a microwave field emitting structure for emitting microwave EM energy carried by the energy conveying structure. That is, all three electrodes may cooperate to emit microwave EM energy.

In an optional embodiment, the first jaw includes a first tooth that projects towards the second jaw (in the open position), the first tooth forming a part of the distal end face.

The first tooth may protrude from a front side of the first jaw or the cutting edge of the first jaw. The front side of the first jaw faces the second jaw in the open position. The first tooth may define a distal end of the cutting edge of the first jaw. Without the first tooth, the cutting edge of the first jaw may extend until the distal end face. The first tooth may be arranged between the distal end face and the cutting edge. In particular, a side surface of the first tooth may define a part of the distal end face. Thus, when viewed along the longitudinal direction on the distal end face of the first jaw, a side surface of the first tooth is visible. The first tooth may be an integral part of the first dielectric planar element. In other words, the first tooth defines a portion of the first jaw.

Optionally, the first tooth is arranged side by side with a distal end face of the second jaw in the closed position of the electrosurgical resector tool. This means that a distal end of the first jaw protrudes distally from a distal end of the second jaw (in the closed position). The first jaw is longer than the second jaw (in the closed position) by a width of the first tooth. In the closed position, the second jaw is at least partially arranged side-by-side with the second jaw, for example the cutting edge of the first jaw overlaps with the cutting edge of the second jaw in the closed position when view from the side. However, the second jaw does not overlap with the first tooth in the closed position due to the shorter longitudinal extension of the second jaw compared to the first jaw.

In an optional embodiment, the first jaw includes a front side facing the second jaw and a rear side facing away from the second jaw, wherein optionally the first pair of electrodes extends on the distal end face to the front side, and/or the first pair of electrodes is spaced apart on the distal end face from the rear side.

The front side of the first jaw may be that side of the first jaw that that is delimited by the cutting edge. For example, the first planar dielectric element includes a front surface, the inner surface, the outer surface, and a rear surface. The front surface of the first planar dielectric element faces towards the second jaw. The front surface of the first planar dielectric element provides a substantial part of the front side; the first pair of electrodes may also contribute to the front side. The first tooth may define a part of the front side. Similarly, the rear side of the first jaw may be partially provided by the rear surface of the first planar dielectric element; the first cover may also contribute to the rear side of the first jaw.

The first pair of electrodes, in particular the inner and outer conductive layers, extend along the cutting edge as a narrow layer. Thus, the first pair of electrodes, in particular the inner and outer conductive layers, do not cover the complete inner and outer surface, respectively, of the first planar dielectric element. However, the first pair of electrodes, in particular the inner and outer conductive layers, may cover the complete area of the first tooth and extend until the distal end face. The first pair of electrodes, in particular the inner and outer conductive layers, extend along the distal end face from the front side to the rear side, wherein there is a gap between first pair of electrodes, in particular the inner and outer conductive layers, and the rear side. This means that the first pair of electrodes, in particular the inner and outer conductive layers, is not exposed at the rear side. This allows that electrosurgical cutting does not take place at the rear side of the first jaw but only at the distal end face, if the electrosurgical resector tool is in the closed position.

The first pair of electrodes, in particular the inner and outer conductive layers, are broader in the area of the first tooth (including the distal end face) compared an area along the cutting edge. The inner conductive layer and/or the outer conductive layer of the first jaw may (completely) cover the first tooth on the inner and/or outer surface. Alternatively, the outer conductive layer of the first jaw does not cover the second tooth on the outer surface.

In an optional embodiment, the movable jaw of the first jaw and the second jaw includes at least one second tooth that projects towards a static jaw of the first jaw and the second jaw, or the second jaw includes at least one second tooth that projects towards the first jaw, wherein optionally the second tooth includes a front surface facing the distal end face and a back surface facing away from a distal end face, and wherein further optionally, in the closed position, the front surface and/or the back surface is tilted towards the distal end face.

The static jaw may be the first jaw and the movable jaw may be the second jaw. However, the static jaw may be the second jaw and the movable jaw may be the first jaw. It is also possible that both the first jaw and the second jaw are movable. Movable defines that the respective jaw is moveable against the base structure or the energy conveying structure.

The second tooth or teeth protrude from the cutting edge of the respective jaw, such as the second jaw. The second tooth may be an integral part of the respective the planar dielectric element, such as the second planar dielectric element. The inner conductive layer and/or the outer conductive layer of the second jaw may (completely) cover the second tooth on the inner surface and/or the outer surface. Alternatively, the outer conductive layer of the second jaw does not cover the second tooth on the outer surface. One of the second teeth may form a part of the distal end face of the second jaw. In particular, all remarks and descriptions on the arrangement of the first tooth equally apply to the second tooth.

The second tooth includes an inner surface (that can be an integral part of the inner surface of the second planar dielectric element), an outer surface (that can be an integral part of the outer surface of the second planar dielectric element), a front surface, and/or a back surface. The front surface of the second tooth may be an integral part of the distal end face for the one of the second teeth that is arranged at the distal end of the second jaw. The front surface and the back surface are opposing surfaces of the second tooth. The front surface and the back surface can be spaced apart from each other in the longitudinal direction of the second jaw.

The front surface and/or the back surface inclined to the longitudinal direction of the second jaw and to the longitudinal direction of the tool tip in the closed position, i.e. when the longitudinal direction of the second jaw is parallel to the longitudinal direction of the tool tip or the first jaw. The angle of inclination may be between 10° and 89°, preferably between 60° and 85°, more preferably between 75° and 85°. This means that the second tooth slightly tilts towards in the distal end of the tool tip. This allows that a front side of the second tooth (the side of the second tooth that is surrounded by the inner surface, the outer surface, the front surface, and the back surface) firstly comes in contact with tissue before one of the inner surface, the outer surface, the front surface, or the back surface comes in contact with the tissue during a movement of the second jaw from the open position to the closed position.

In an optional embodiment, the electrosurgical resector tool further comprises a control wire for actuating the movable jaw of the first jaw and the second jaw, wherein optionally the movable jaw includes an opening through which the control wire extends for engagement with the movable jaw, and wherein further optionally an end of the control wire is rounded. Alternatively or additionally, the control wire is bent.

The control wire may be an example of the actuator described above. The control wire is coupled to the movable jaw such a pulling or pushing movement of the control wire results in a movement of the movable jaw, for example from the closed position to the open position or vice versa. The control wire may be coupled to the movable jaw by means of the opening; a part of the control wire extends through the opening. The opening may be a through hole in the second jaw. The opening may be arranged in the second cover. The opening may have a direction of extension that is perpendicular to the longitudinal direction along which to control wire extends through the shaft. Thus, the control wire may include a bending. Preferably, the control wire includes only a single bending from the direction of extension in the shaft to the direction of the opening. This may be a 90° bending. Alternatively, the control wire includes two bendings or bends (e.g. corner or angle portions). The first bending connects the direction of extension of the control wire in the shaft to the direction of extension of the control wire in the opening. The second bending is located between the end of the control wire and the opening. The first bending and/or the second bending may be 90° bending. The end of the control wire may extend in a plane parallel to the extension of the control wire in the shaft. In particular, the first bending and the second bending have a S-shape in a side view. The second bending can prevent the end of the wire from being pulled through the opening. Thus, the second bending may act as an abutment.

An inner diameter of the opening may be greater than an outer diameter of the control wire. Thus, the control wire can move relative to the opening in the absence of the rounded end of the control wire or the second bending. The rounded end reduces the risk that the end of the control wire interlocks with or sticks to tissue or with other parts of the electrosurgical resector tool.

In an optional embodiment, the rounded end of the control wire has a diameter that is larger than an inner diameter of the opening.

The control wire may be rounded by welding, in particular laser welding, which results in a rounded end having a diameter greater than the diameter of the control wire and the inner diameter of the opening. The control wire is rounded after insertion into the opening. This provides a fixation of the control wire in the opening between the rounded end and the bending in the control wire.

In an optional embodiment, the movable jaw includes a chamfered portion adjacent to the opening, wherein optionally the rounded end of the control wire is at least partially arranged within the chamfered portion.

The chamfered portion may have a funnel shape and in fluid communication with the opening. The chamfered portion may constitute a gradual extension of the diameter of the opening from the inner diameter to the opening to an increased diameter at the surface of the second cover. The rounded end of the control wire may be partially received in the chamfered portion which may result in that only small part of the rounded end protrudes from the second cover. This further reduces the risk that the control wire accidentally engages with tissue or other parts of the electrosurgical resector tool.

In an optional embodiment, the planar dielectric element of the static jaw of the first jaw and the second jaw extends to the distal end of the energy conveying structure, wherein optionally the tool tip further comprises a connection element connecting the inner conductor of the energy conveying structure to the inner electrode of the first pair of electrodes and/or a dielectric block arranged between the movable jaw of the first jaw and the second jaw and the distal end of the energy conveying structure. The connection element is optionally sandwiched between the planar dielectric element of the static jaw and the dielectric block, wherein optionally the dielectric block is attached to the planar dielectric element of the static jaw using an adhesive preferably including an adhesive component and particles immersed in the adhesive component.

The planar dielectric element of the static jaw, optionally the first jaw, can include a part defining the first jaw and a part defining the connecting portion, Thus, the first planar dielectric element of the first jaw and the connecting portion may be considered a section of an integral component. The part defining the first jaw may have a length in the longitudinal direction that corresponds to the first pair of electrodes, while the connecting portion is the part of the (first) planar dielectric element that extends towards the energy conveying structure.

The connection element may extend on the connecting portion of the planar dielectric element, while the inner and/or outer conductive layers arranged on the part of the (first) planar dielectric element defining the first jaw. The connection element may be an integral component with inner conductive layer and, thus, may be manufactured from the same materials as the inner conductive layer. The connection element may be electrically connected to the inner conductor of the energy conveying structure.

The dielectric block is made from a dielectric material, such as a ceramic including alumina, and can be made from the same dielectric material as the first and/or second planar dielectric element. The dielectric block is arranged in the longitudinal direction between the movable (second) jaw and the energy conveying structure. The dielectric block provides a barrier between the movable jaw and the energy conveying structure. The dielectric block may have a height that corresponds to the height of the movable jaw. The first planar dielectric element and the dielectric block sandwich the connection element there between. The first planar dielectric element and the dielectric block may be surrounded by a sleeve or conductive ring.

The dielectric block may be glued to the first planar dielectric element using an adhesive that is used in dentistry, for example for attaching a crown to a tooth. The adhesive may be G-CEM linkace, 3M™ RelyX™ Ultimate, or 3M™ RelyX™ Ultimate 2. The adhesive can include an adhesive component providing the adhesive characteristics of the adhesive. The adhesive component may (UV) light curable. The adhesive component may include a monomer providing the adhesive characteristics by polymerisation of the monomer. The adhesive component may include diurethanedimethacrylate.

The adhesive may include one or more fillers such as Ytterbium (III) fluoride. Particles made from dielectric, polymer, and/or ceramic material are immersed in the adhesive component. The particles have an average diameter in the micro millimeter range and/or nano meter range, for example between 50 nm or 100 nm to 50 µm to 100 µm. The particles may include glass powder. The surface of the (glass powder) particles may be modified. The particles provide the mechanical and electrical properties of the adhesive.

For example, the particles are less susceptible to plasma (such as sparks) generated close to the electrodes compared to the adhesive component. Thus, the particles reduce degeneration of the adhesive resulting in a more stable adhesion of the dielectric block to the first planar dielectric element.

In an optional embodiment, a cavity is provided between the dielectric block and the distal end of the energy conveying structure, wherein optionally the cavity is filled with the adhesive.

The cavity may be the cavity as described above. The adhesive can be used instead of the potting material and is an example of the dielectric material with which the cavity can be filled. The adhesive helps to (initially) attach the first base part, the second base part, and the dielectric block to each other. The first base part, the second base part, and the dielectric block can be permanently fixed to each other by the sleeve or conductive ring which is pushed over the first base part and the second base part and, thus, surrounds the first base part and the second base part.

The tool tip may be dimensioned to fit within an instrument channel of a surgical scoping device. Accordingly, in another aspect, an electrosurgical apparatus is provided which comprises: an electrosurgical generator for supplying radiofrequency (RF) electromagnetic (EM) energy and microwave EM energy; a surgical scoping device having an instrument cord for insertion into a patient's body, the instrument cord having an instrument channel extending therethrough; and an electrosurgical resector tool as described above inserted through the instrument channel of the surgical scoping device.

The apparatus may comprise a handpiece for controlling the electrosurgical resector tool. The handpiece may be mounted at a proximal end of the shaft, e.g. outside the surgical scoping device.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial transmission line. The term "outer" means radially further from the centre (axis) of the instrument channel and/or coaxial transmission line.

The term "conductive" is used herein to mean electrically conductive, unless the context dictates otherwise.

Herein, the terms "proximal" and "distal" refer to the ends of the elongate tool. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHZ. Specific frequencies that have been considered are: 915 MHZ, 2.45 GHZ, 3.3 GHZ, 5.8 GHZ, 10 GHZ, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHZ, and most preferably 400 KHz.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
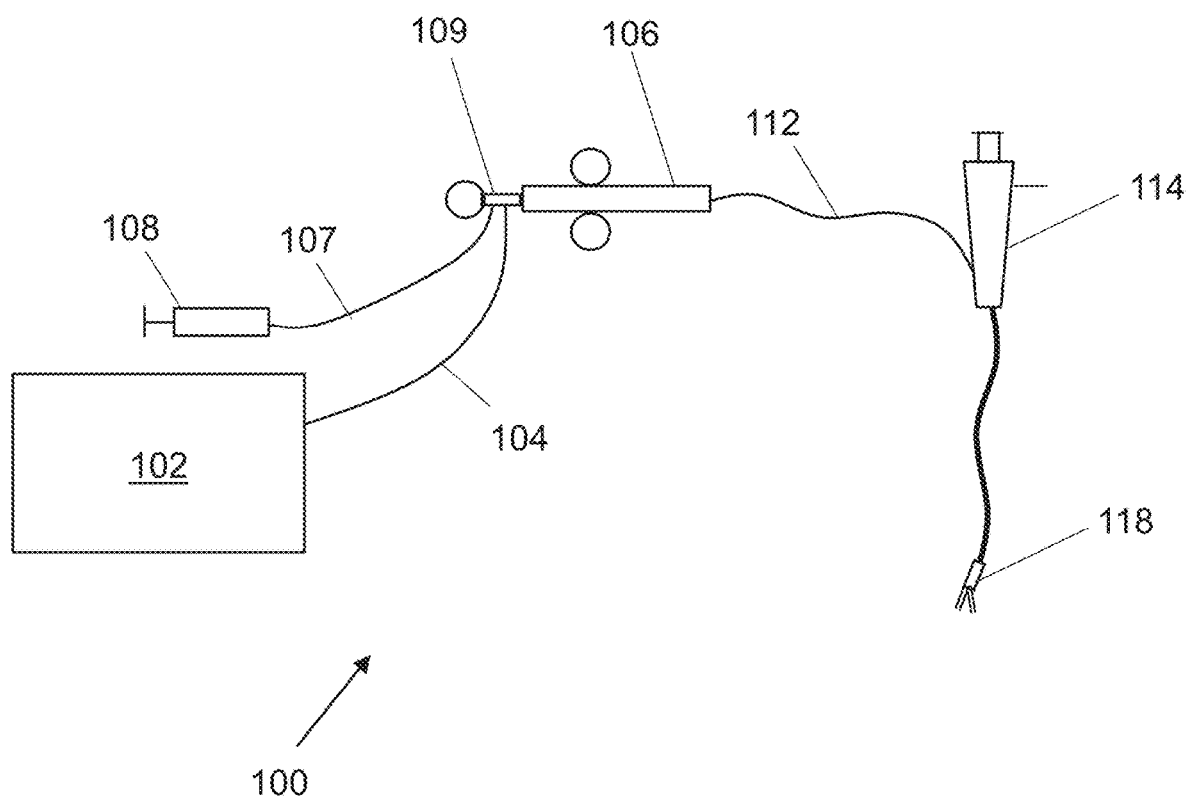
FIG. 1 is a schematic diagram of an electrosurgical system that is an embodiment of the present invention.

FIG. 1 is a schematic diagram of an electrosurgical system 100 that is an embodiment of the invention. The system 100 is arranged to treat (e.g. cut or seal) biological tissue using radiofrequency (RF) or microwave electromagnetic (EM) energy from an tool tip 118. The system 100 comprises a generator 102 for controllably supplying the RF and microwave EM energy. A suitable generator for this purpose is described in WO 2012/076844, which is incorporated herein by reference. The generator 102 is connected to a handpiece 106 by an interface cable 104. The handpiece 106 may also be connected to receive a fluid supply 107 from a fluid delivery device 108, such as a syringe, although this is not essential. If needed, the handpiece 106 may house an tool actuation mechanism that is operable by an actuator 109, e.g. a thumb operated slider or plunger. For example the tool actuation mechanism may be used to operate opening and closing of jaws of a resector tool, as discussed herein. Other mechanisms may also be included in the handpiece. For example, a needle movement mechanism may be provided (operable by a suitable trigger on the handpiece) for deploying a needle at the tool tip 118. A function of the handpiece 106 is to combine the inputs from the generator 102, fluid delivery device 108 and tool actuation mechanism, together with any other inputs which may be required, into a single flexible shaft 112, which extends from the distal end of the handpiece 106.

The flexible shaft 112 is insertable through the entire length of an instrument (working) channel of a surgical scoping device 114. The flexible shaft 112 has an tool tip 118 that is shaped to pass through the instrument channel of the surgical scoping device 114 and protrude (e.g. inside the patient) at the distal end of the endoscope's insertion tube. The tool tip 118 includes a pair of jaws having blade elements for gripping and cutting biological tissue, and an energy delivery structure arranged to deliver RF or microwave EM energy conveyed from the generator 102. Optionally the tool tip 118 may also include a retractable hypodermic needle for delivering fluid conveyed from the fluid delivery device 108. The handpiece 106 includes an actuation mechanism for opening and closing the jaws of the tool tip 118. The handpiece 106 may also include a rotation mechanism for rotating the tool tip 118 relative to the instrument channel of the surgical scoping device 114.

The structure of the tool tip 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The flexible shaft 112 may have a maximum diameter less than this, e.g. 2.65 mm. The length of the flexible shaft 112 can be equal to or greater than 1.2 m, e.g. 2 m or more. In other examples, the tool tip 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114. The system described above is one way of introducing the tool into a patient. Other techniques are possible. For example, the tool may also be inserted using a catheter.

Although the examples herein are present in the context of a surgical scoping device, it is to be understood that the electrosurgical resector tool may be embodied in a device suitable for open surgery or use with a laparoscope.

Figure 2:
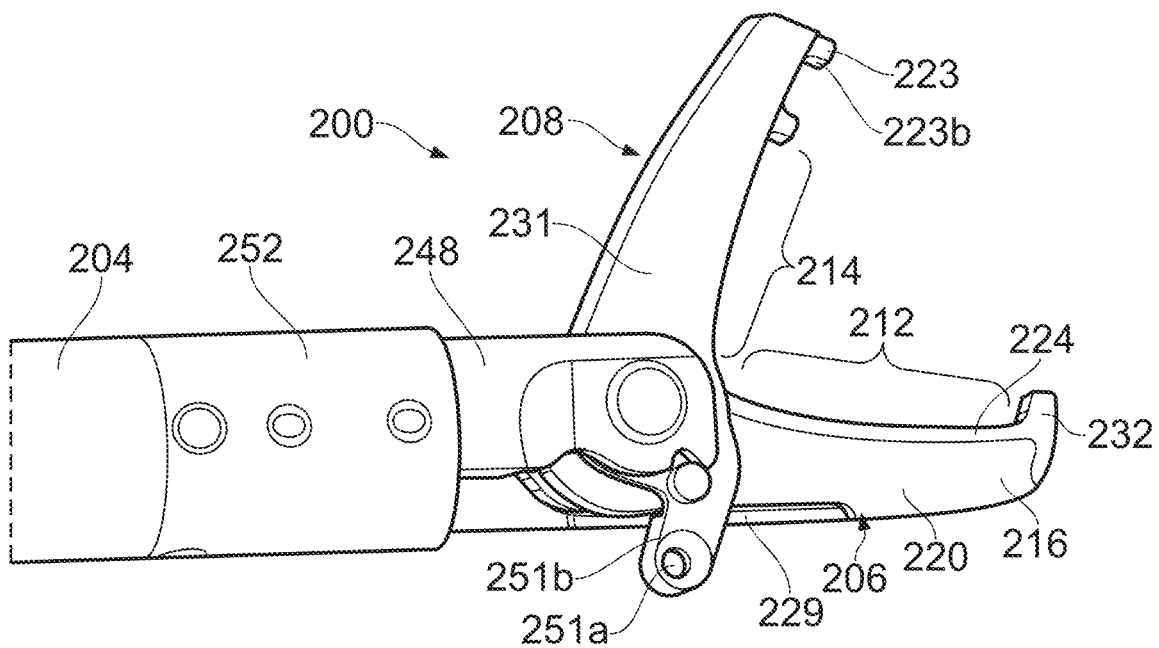
FIG. 2 is a perspective view of an electrosurgical resector tool in an open position according to an embodiment of the invention.
Figure 8:
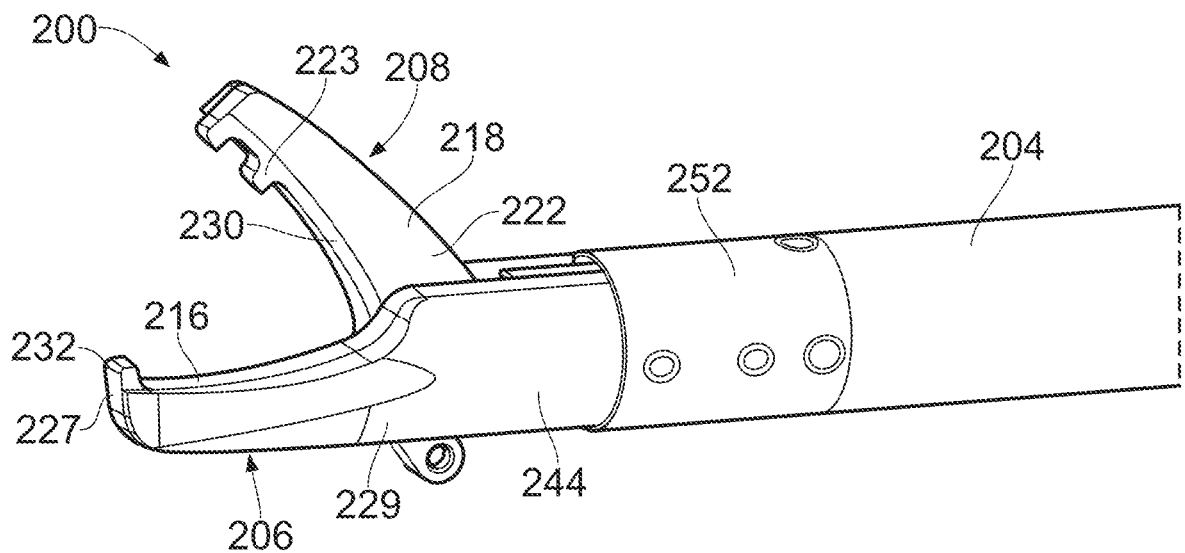
FIG. 8 is another perspective view of the electrosurgical resector tool of FIG. 2 in an intermediate position.
Figure 9:
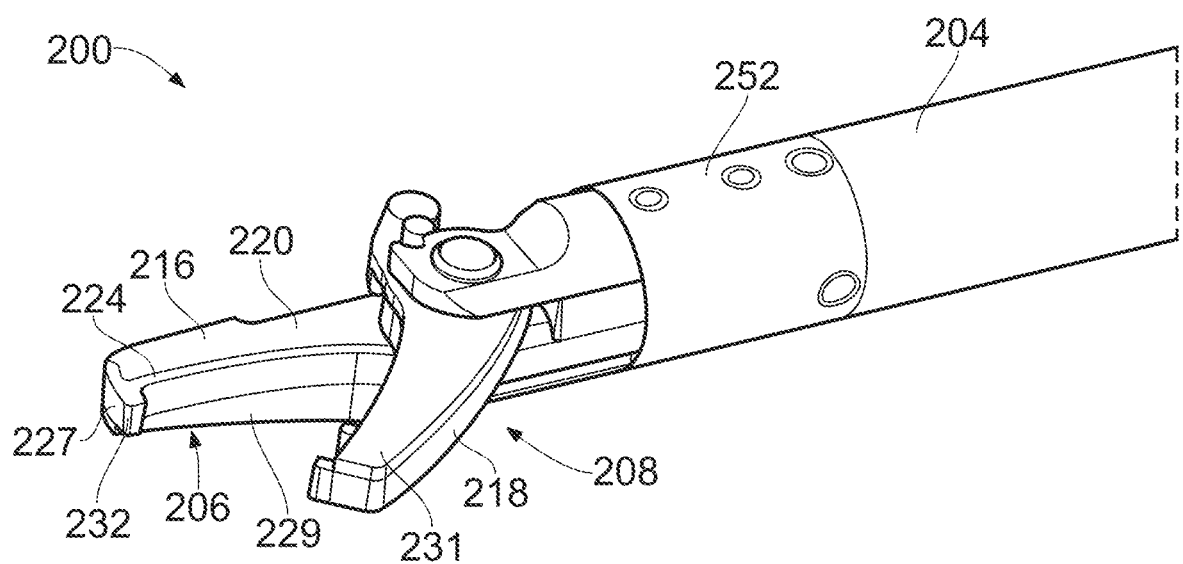
FIG. 9 is a further perspective view of the electrosurgical resector tool of FIG. 2 in an intermediate position.
Figure 12:
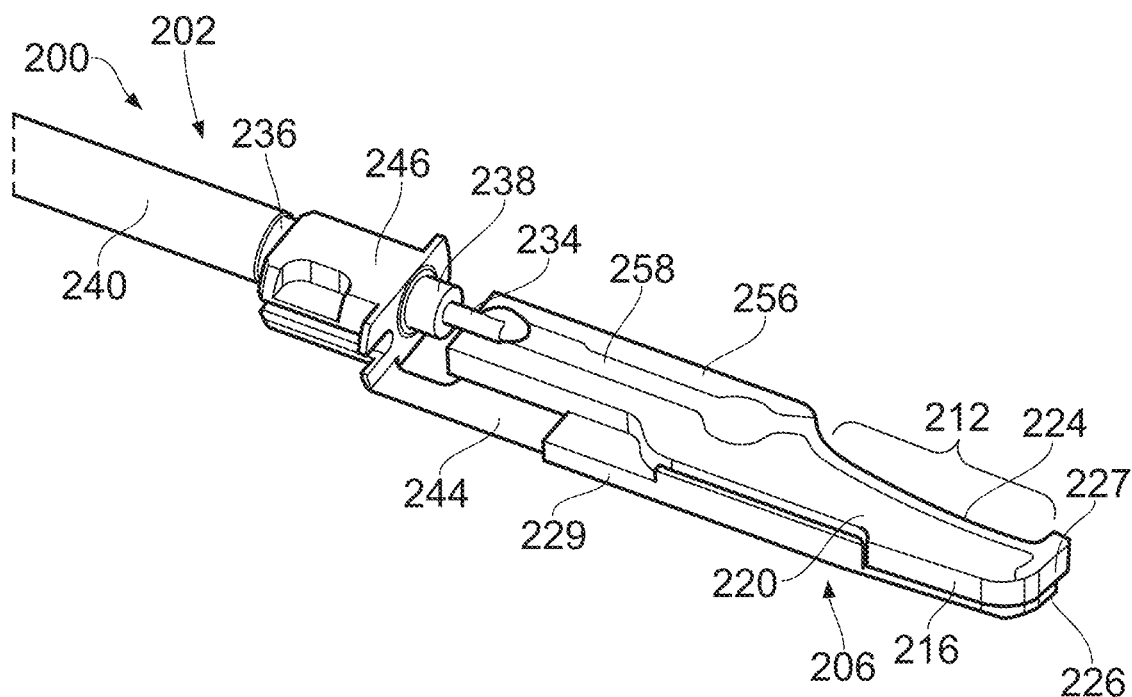
FIG. 12 is a perspective view depicting parts of the electrosurgical resector tool prior to assembly.
Figure 13:
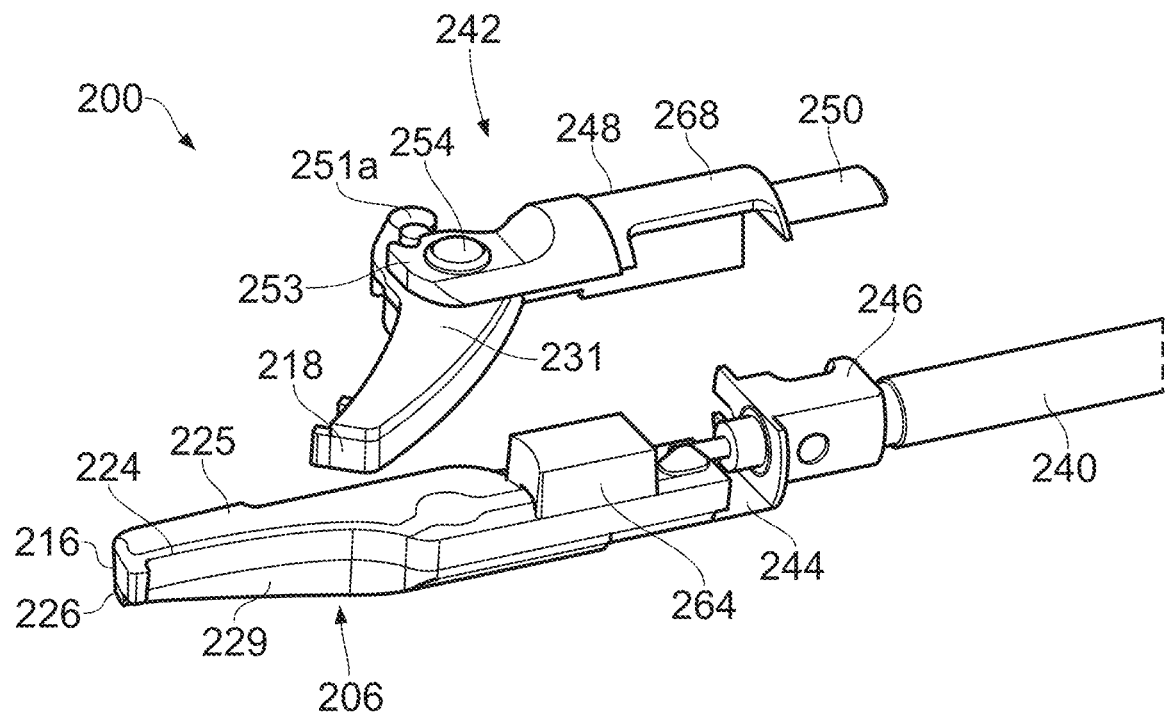
FIG. 13 is a perspective exploded view depicting parts of the electrosurgical resector tool of FIG. 12 prior to assembly.
Figure 14:
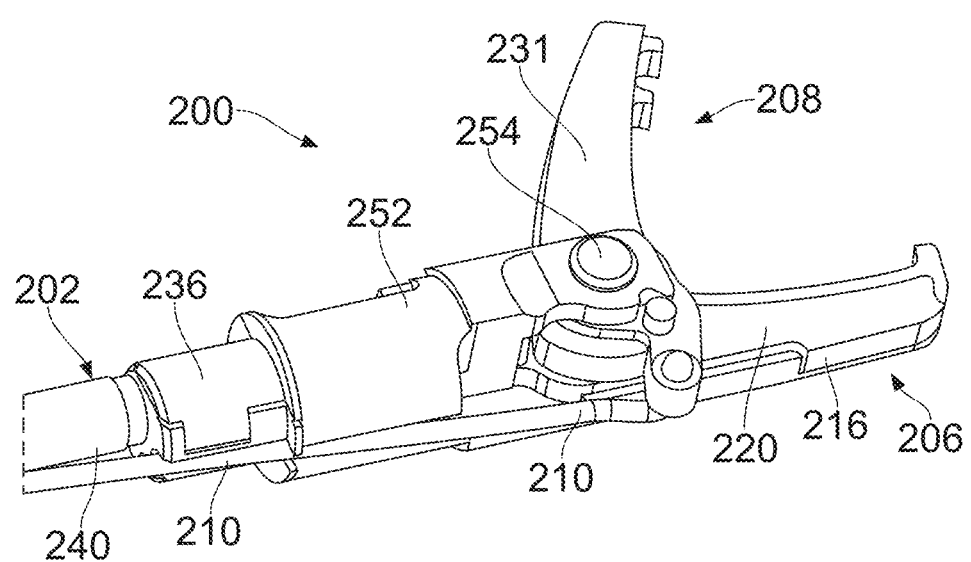
FIG. 14 is a perspective exploded view depicting parts of the electrosurgical resector tool of FIG. 12, prior to complete assembly.

FIGS. 2 to 11 illustrate an tool tip 200 of an electrosurgical resector tool that is an embodiment of the invention. The tool tip 200 may, for example, correspond to the tool tip 118 discussed above in relation to FIG. 1. FIG. 2 shows a first schematic view of a first side of the tool tip 200, depicting a first side of the tool tip 200, and FIGS. 8 and 9 show schematic views of a second side of the tool tip 200. FIGS. 12-14 illustrate a construction of another embodiment of the tool tip 200 which is provided to illustrate certain features of the tool tip 200 of FIGS. 2 to 11.

The tool tip 200 is mounted at a distal end of an energy conveying structure, which is in the form of a coaxial cable 202 (shown in FIGS. 12-14). The coaxial cable 202 extends through a flexible shaft 204, which may correspond to the flexible shaft 112 discussed above. In particular, the flexible shaft 204 defines a lumen through which the coaxial cable 202 extends, with the tool tip 200 protruding from a distal end of the flexible shaft 204. The coaxial cable 202 is arranged to convey RF and microwave EM energy to the tool tip 200 from an electrosurgical generator (e.g. generator 102 mentioned above).

The tool tip 200 has a first jaw 206 and a second jaw 208 which are movable relative to one another between an open position and a closed position. Specifically, in the example shown, the first jaw 206 is static, i.e. it is fixed relative to the distal end of the coaxial cable 202, whilst the second jaw 208 is pivotably mounted to the first jaw 208. The first jaw 206 can be considered a static or fixed jaw and the second jaw 208 can be considered a movable jaw. However, the invention is not limited thereto. The second jaw 208 can be the static jaw and the first jaw 206 can be the movable jaw.

An actuator in the form of a control wire or (or rod) 210 is connected to the second jaw 208 (see e.g. FIGS. 3 and 14), in order to control movement of the second jaw 208 relative to the first jaw 206. The control wire 210 is disposed within the lumen of the flexible shaft 204 and is longitudinally slidable within the lumen to move the second jaw 208. A proximal end of the control wire 210 may be connected to a handpiece (e.g. handpiece 106), which is operable to control movement of the second jaw 208 via the control wire 210. FIG. 2 depicts the jaws 206, 208 in the open position, where a gap is defined between the jaws 206, 208 in which tissue can be received. FIGS. 4 to 7 depict the jaws 206, 208 in a closed position, where there is no gap between the jaws 206, 208 and the jaws 206, 208 extend parallel to each other. FIGS. 3 and 8 to 11 depict intermediate position which are positions between the (fully) open position and the closed position.

The first jaw 206 comprises a first blade element 212, and the second jaw 208 comprises a second blade element 214. Each blade element may comprise an edge which is arranged to contact tissue located in the gap between the jaws, and to cut the tissue when the jaws are moved to the closed position. Specifically, the second blade element 214 is arranged to slide across the first blade element 212 when the second jaw 208 is moved towards the closed position, such that a shearing force is applied to tissue located in the gap between the jaws 206, 208. Thus, tissue located in the gap between the jaws can be cut by pivoting the second jaw 208 towards the closed position.

The first blade element 212 is defined by a first planar dielectric element 216 in the first jaw 206, and the second blade element 214 is defined by a second planar dielectric element 218 in the second jaw 208. In particular, the first planar dielectric element 216 includes an inner surface 220 that faces towards the second planar dielectric element 218 in the closed position, and across which an inner surface 222 of the second planar dielectric element 218 slides when the second jaw 208 is pivoted relative to the first jaw 206, such that there is a shearing motion between the two planar dielectric elements. Each of the first and second planar dielectric elements 216, 218 may be made from ceramic (e.g. alumina) or other suitable electrically insulating material. The first and second planar dielectric elements 216, 218 each define a plane which is parallel to a plane through which the second jaw 208 pivots relative to the first jaw 206.

The second planar dielectric element 218 includes a pair of projections (or second teeth) 223, which act as serrations for the second blade element 214. Thus, the second teeth 223 may serve to grip tissue located in the gap between the jaws, to facilitate holding and/or cutting the tissue. The first planar dielectric element 216 may include similar projections (not shown), to act as serrations for the first blade element 212. The second teeth 223 include a front surface 223a and a back surface 223b. The back surface 223b faces towards the flexible shaft 204 in the closed position. The front surface 223a is the opposite site compared to the back surface 223b and faces away from the flexible shaft 204 in the closed position. In other words, the front surface 223a faces towards a distal end face 227 of the tool tip 200, while the back surface 223b faces away from the distal end face 227. In the closed position, the front surface 223a and/or the back surface 223b are tilted relative to a direction of extension of the tool tip 200. The front surface 223a and/or the back surface 223b define an angle of less than 90° with the direction of extension of the tool tip 200. The second teeth 223 are forward facing for better tissue engagement when going face on to flat tissue. A surface of the second teeth 223 that faces the first jaw 206 and is arranged between the front surface 223a and the back surface 223b firstly contacts the tissue compared to the front surface 223a.

In one embodiment, the tool tip 200 comprises two electrodes for delivering energy to tissue, wherein one of the jaws 206, 208 comprises a pair of electrodes and the other jaw 206, 208 comprises no electrode. In another embodiment, the tool tip 200 comprises three electrodes for delivering energy to tissue, wherein one jaw 206, 208 comprises a pair of electrodes and the other jaw 206, 208 comprises a single electrode.

In a further embodiment which is shown in the figures, the first jaw 206 includes an inner electrode 224 formed on the inner surface 220 of the first planar dielectric element 216, and an outer electrode 226 arranged on an outer surface of the first planar dielectric element 216. Thus, the first planar dielectric element 216 serves to electrically isolate the inner electrode 224 from the outer electrode 226 of the first jaw 206 from one another. The inner electrode 224 and/or the outer electrode 226 can include a conductive layer deposited onto the first planar dielectric element 216. The outer electrode 226 may also include a first cover 229 made from an electrically conductive material, such as metal (e.g. steel), or from an electrically non-conductive material. The first cover 229 covers the conductive layer of the outer electrode 226 and/or the first planar dielectric element 216. Optionally, the first cover 229 covers the complete first planar dielectric element 216.

The second jaw 208 includes an outer electrode 228 formed on the outer surface of the second planar dielectric element 218, and an inner electrode 230 arranged on an inner surface of the second planar dielectric element 218. Thus, the second planar dielectric element 218 serves to electrically isolate the inner electrode 230 from the outer electrode 228 of the first jaw 208 from one another. The inner electrode 230 and/or the outer electrode 228 can include a conductive layer deposited onto the second planar dielectric element 218. The outer electrode 228 may also include a second cover 231 made from an electrically conductive material, such as metal (e.g. steel), or from an electrically non-conductive material. The second cover 231 covers the conductive layer of outer electrode 228 and/or the second planar dielectric element 218. Optionally, the second cover 231 covers the complete second planar dielectric element 218. The inner electrode 224 of the first planar dielectric element 216 contacts the inner electrode 230 of the second planar dielectric element 218 in the open and/or the closed position.

Of course, in some embodiments, a single electrode may be formed on an inner surface 222 of the second jaw 208, wherein the first jaw 206 may advantageously comprise a dielectric coating, or a third planar dielectric element, formed on the inner electrode 224 and the inner surface 220 of the first planar dielectric element 216, to ensure that when the jaws are closed, there is no electrical connection between the inner electrode 224 and the single electrode of the second jaw. However, the third dielectric planar element or coating material may be arranged such that the inner electrode 224 is exposed along the top face of the first jaw 206 to ensure that RF and/or microwave energy may be emitted therefrom as described below with respect to FIGS. 21 and 22. This coating, or third planar dielectric element, thereby serves to electrically isolate the inner electrode 224 of the first jaw 206 and the inner electrode 228 of the second jaw 208 from one another. However, where the single electrode is an outer electrode 228, the second planar dielectric element 218 serves to ensure that there is no electrical connection with the inner electrode 224 of the first jaw.

The inner electrode 224 of the first jaw 206 and/or the inner electrode 230 of the second jaw 208 can include a layer or film of conductive material (e.g. gold), which is deposited on the inner surface 220 of the first planar dielectric element 216 and the inner surface 222 of the second planar dielectric element 216, respectively. The inner electrode 224 and/or the inner electrode 230 cover part of this inner surface 220 and the inner surface 222, respectively, and extend along a cutting edge of the first blade element 212 (i.e. of the first planar dielectric element 216) and the second blade element 214 (i.e. of the second planar dielectric element 218), respectively.

The outer electrode 226 of the first jaw 206 and/or the outer electrode 228 of the second jaw 208 can include a layer or film of conductive material (e.g. gold), which is deposited on the outer surface of the first planar dielectric element 216 and the outer surface of the second planar dielectric element 216, respectively. The conductive layer of the outer electrode 226 of the first jaw 206 can be sandwiched between the first planar dielectric element 216 and the first cover 229. The conductive layer of the outer electrode 228 of the second jaw 208 can be sandwiched between the second planar dielectric element 218 and the second cover 231.

The one of the first jaw 206 or the second jaw 208 which includes the first pair of electrodes is longer that the other jaw 206, 208 in the closed position. In the embodiment depicted in FIGS. 2 to 11, the first jaw 206 is longer than the second jaw 208 in the closed position. Thus, the first jaw 206 extends beyond the second jaw 208 in the closed position. The distal end face 227 of the first jaw 206 is the most distal surface of the tool tip 200. The inner electrode 224 and the outer electrode 226, in particular the conductive layers thereof, of the first jaw 206 extend along the distal end face 227. For example, the inner electrode 224 and the outer electrode 226 are flush with the distal end face such that, when the distal end face contacts tissue, the inner electrode 224 and the outer electrode 226 also contact the tissue.

The longer one of the first and second jaws 206, 208 includes a first tooth 232 which protrudes towards the shorter one of the first and second jaws 206, 208. In the embodiment depicted in FIGS. 2 to 11, the first tooth 232 is arranged on the first jaw 206. Optionally, first jaw 206 is longer than the second jaw 208 by the width of the first tooth 232 in the direction of the first jaw 206. Thus, in the closed position, the first tooth 232 is not covered by the second jaw 232. The first tooth 232 may be in an integral part of the first planar dielectric element 216.

The first jaw 206 can include a front side which faces the second jaw 208 and a rear side which faces away from the second jaw 208. The cutting edge can be the edge on the front side. The front side and/or the rear side may be provided by the inner electrode 220, the first planar dielectric element 216, the outer electrode 222, and/or the first cover 231.

The inner electrode 224 and the outer electrode 226, in particular the conductive layers thereof, extend along the distal end face 227 until the front side of the first tooth 232. The front side of the first tooth 232 may be that surface which face towards the second jaw 208 and is adjacent to the first distal end face 227. The first tooth 232 can define the distal end of the cutting edge of the first blade element 212. The inner electrode 224, in particular the conductive layer thereof, can cover the complete area of the inner surface 220 of the first planar dielectric element 216 which corresponds to the first tooth 232. The outer electrode 226, in particular the conductive layer thereof, can cover the complete area of the outer surface 222 of the first planar dielectric element 216 which corresponds to the first tooth 232.

The inner electrode 224 and the outer electrode 226, in particular the conductive layers thereof, extend along the distal end face 227 towards the rear side of the first jaw 206 but terminate spaced apart from the rear side. The inner electrode 224 and the outer electrode 226, in particular the conductive layers thereof, are not in contact or flush with the rear side. There is a gap between the conductive layers of the inner electrode 224/the outer electrode 226 and the rear side. Thus, tissue in contact with the rear side is not in contact with the conductive layers of the inner electrode 224 and the outer electrode 226.

The first cover 229 can be in the form of a first conductive shell which is attached (e.g. glued) to the outer surface of the first planar dielectric element 216. The first cover 229 can be a piece of conductive material which covers the entire outer surface of the first planar dielectric element 216, and which has a thickness that is similar to a thickness of the first planar dielectric element 216. An outer surface of the first cover 229 acts an outer surface of the first jaw 206. The outer surface of the first cover 229 may be rounded, so that the first jaw 206 has a smooth outer surface. The first cover 229 may comprise a protrusion which is shaped to engage with a groove formed in the first dielectric element 216 to avoid slippage between the two parts, and ensure that the parts are correctly oriented with respect to one another.

The inner and/or outer electrodes 228, 230 of the second jaw 208 may be formed in a similar manner to the inner electrode 224 and/or the outer electrode 226 of the first jaw 206. For example, the inner and outer electrodes 228, 230 of the second jaw 208 may include a layer or film of conductive material (e.g. gold), which is deposited on the inner surface 222 and outer surface, respectively, of the second planar dielectric element 218. The conductive layer of the inner electrode 230 thereby covers part of the inner surface 222, and extends along a cutting edge of the second blade element 214 (i.e. of the second planar dielectric element 218), such that it is located at the cutting interface between the first and second blade elements when the jaws are closed. In such embodiments, the outer surface of the second jaw 208 is formed by an outer surface of the second planar dielectric element 218, which may be rounded so that the second jaw 208 has a smooth outer surface. The conductive layer of the outer electrode 228 can be covered by the second cover 231 which is in the form of a second conductive shell which is attached (e.g.) glued to the outer surface of the second planar dielectric element 218, and which has a thickness that is similar to a thickness of the second planar dielectric element 218.

The four electrodes 224, 226, 228, 230 are electrically connected to the distal end of the coaxial cable 202, so that the electrodes can deliver RF and microwave EM energy conveyed by the coaxial cable 202. The manner in which the electrodes are connected to the coaxial cable 202 is discussed in more detail below.

Figure 10:
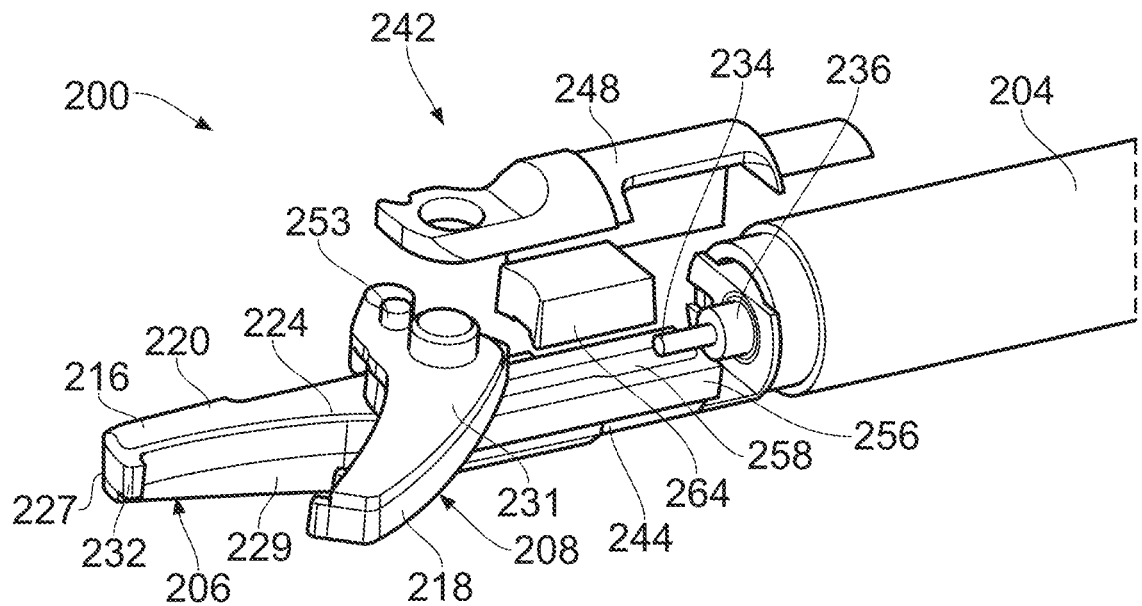
FIG. 10 is an exploded view of the electrosurgical resector tool of FIG. 2 in an intermediate position.
Figure 11:
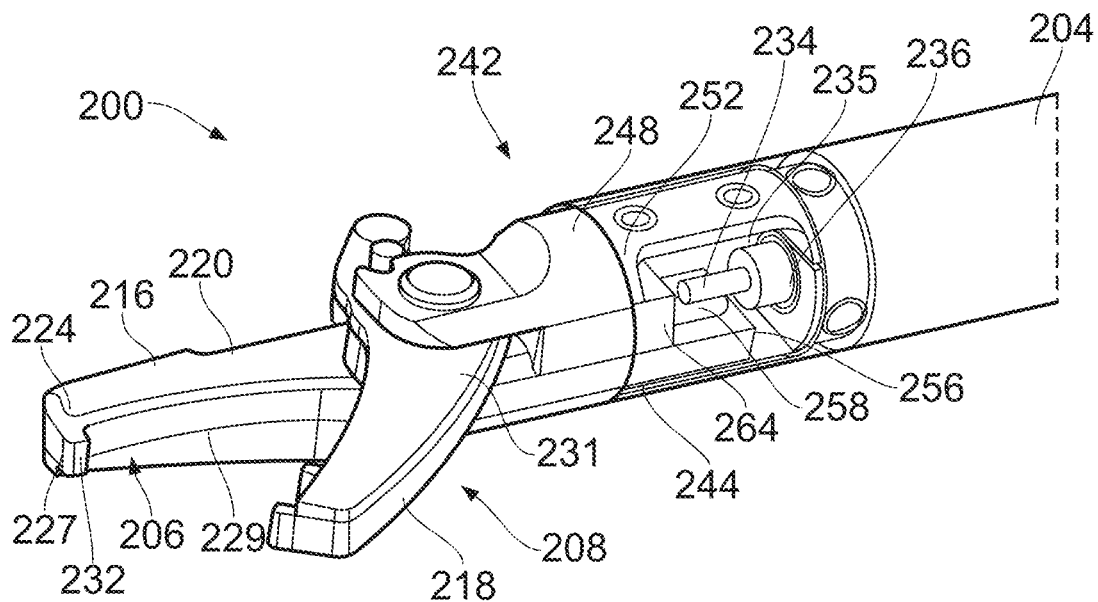
FIG. 11 is the perspective view of the electrosurgical resector tool of FIG. 9 with a conductive ring made visible.

As visible in FIGS. 10 and 12, the tool tip 200 includes a connection element 258 and a dielectric block 264. The connection element 258 can be a wire and extends longitudinally along a connecting portion 256 of the first planar dielectric element 216, to electrically connect the inner electrode 224 to the distal end of an inner conductor 234. The connection element 258 may be a part of the inner electrode 224 which extends along the connecting portion 256, e.g. the connection element 258 and inner electrode 224 may be deposited together on the inner surface 220 of the first planar dielectric element 216. The inner electrode 230 of the second jaw 208 may be in electrical sliding contact with the connection element 258, i.e. the inner electrode 230 of the second jaw 208 slides on the connection element 258 when the second jaw 208 is moved between the first position and the second position.

The dielectric block 264 is mounted between a second base part 248 and the first planar dielectric element 216 (in particular the connecting portion 256), in order to avoid electrical breakdown between the connection element 258 and the conductive second base part 248. For example, the dielectric block 264 may be made of a ceramic material, such as alumina. The connection element 258 is sandwiched between the dielectric block 264 and the connecting portion 256. The dielectric block 264 may be secured in place using an adhesive which can be include an adhesive component and particles immersed in the adhesive component. The particles may be made from a dielectric or ceramic material such as alumina or glass. The particles reduce the degeneration of the adhesive due to plasma generated by the electrodes 224, 226, 228, 230.

A cavity 235 is formed between a first base part 244 and a second base part 248 (described later), in which the inner conductor 234 is electrically connected to the connection element 258 (and thus to the inner electrodes 224, 230). The cavity 235 may be filled with a dielectric material, such as a potting material, or the adhesive described above, in order to reduce the risk of electrical breakdown between the distal end of the inner conductor 234 and the base structure 242. Filling the cavity 235 with a dielectric material or the adhesive may also serve to reinforce the tool tip 200, and hold the first and second base parts 244, 248 together. The second base part 248 may include an injection port via which dielectric material or the adhesive can be injected into the cavity 235. The particles in the adhesive provide dielectric properties similar to the dielectric material.

A construction of the tool tip 200 is now discussed with reference to FIGS. 12 to 14, which depict various stages of assembly of the tool tip 200.

The coaxial cable 202 includes the inner conductor 234 and an outer conductor 236 which are separated by a dielectric material 238. Additionally, the coaxial cable 202 includes an outer sheath 240 which is made of an insulating material. The first jaw 206 and the second jaw 208 are mounted to the distal end of the coaxial cable 202 via a base structure 242. The base structure 242 includes a first base part 244 made of a conductive material, which rigidly connects the first jaw 206 to the distal end of the coaxial cable 202. The first base part 244 comprises an arm which extends between the distal end of the coaxial cable 202 and the first cover 229. In the example shown, the first cover 229 and the first base part 244 are integrally formed as a single piece of conductive material. However, in other examples, they may be formed as separate parts that are connected together. The first base part 244 includes a first mounting portion 246 that includes a channel in which the distal end of the coaxial cable 202 is received. A length of the outer sheath 240 of the coaxial cable 202 is removed in the vicinity of the distal end of the coaxial cable, so that the outer conductor 236 is exposed. The outer conductor 236 is thus in electrical contact with the first base part 244 in the channel in the first mounting portion 246. The distal end of the coaxial cable 202 may be secured in the channel in the first mounting portion 246 using a suitable conductive epoxy. As a result, the first cover 229 (and thus the outer electrodes 226, 228 of the first and second jaws 206, 208) is electrically connected to the outer conductor 236 via the first base part 244.

The base structure 242 further comprises a second base part 248, which pivotably mounts the second jaw 208 to the distal end of the coaxial cable 202. The second base part 248 is made of a conductive material, which may be the same material as the first base part 244 (e.g. stainless steel). The second base part 248 includes a second mounting portion 250 which is secured to the first mounting portion 246 on the first base part 244, such that the first base part 244 and the second base part 248 are in electrical contact. The first mounting portion 246 and the second mounting portion 250 have complimentarily shaped engagement surfaces which are engaged with one another when the base parts are secured together. As shown in FIG. 14, the first base part 244 and the second base part 248 are secured together via a conductive ring 252 that fits around the first and second mounting portions 246, 250 to hold them together. An adhesive (such as the one described above) may be injected inside the conductive ring 252, in order to secure the conductive ring 252 in place over the first and second mounting portions. In addition to holding the base structure 242 together, the conductive ring 252 may act as a microwave shield, which prevents microwave energy from being radiated prior to reaching the electrodes in the jaws.

The second base part 248 includes an arm that extends longitudinally from the second mounting portion 250, and to which the second jaw 208 is pivotably mounted. In the example shown, the second jaw 208 pivotably mounted to the second base part 240 via a rivet 254. The outer electrode 228, in particular the second cover 231, is in electrical contact with the second base part 248 via the rivet 254 (which is made of a conductive material). Thus, the outer electrode 228 on the second jaw 208 is electrically connected to the outer conductor 236 of the coaxial cable 202, via a conductive pathway formed of the rivet 254, the second base part 248, the mounting portion 246 and the first base part 244. Accordingly, both the outer electrode 226 of the first jaw 206 and the outer electrode 228 of the second jaw 208 are electrically connected to the outer conductor 236 via the base structure 242.

The second base part 248 may include a passageway (not shown) through which the control wire 210 extends to connect to the second jaw 208. The second cover 231 may include an opening 251a, through which a distal end of the control wire 210 extends. The second cover 231 shell may also be provided with a limiting pin 253 (shown in FIG. 13), which serves to limit motion of the second jaw 208 relative to the first jaw 206 between the open and closed positions. This may enable the position of the second jaw 208 to be controlled more accurately.

Figure 3:
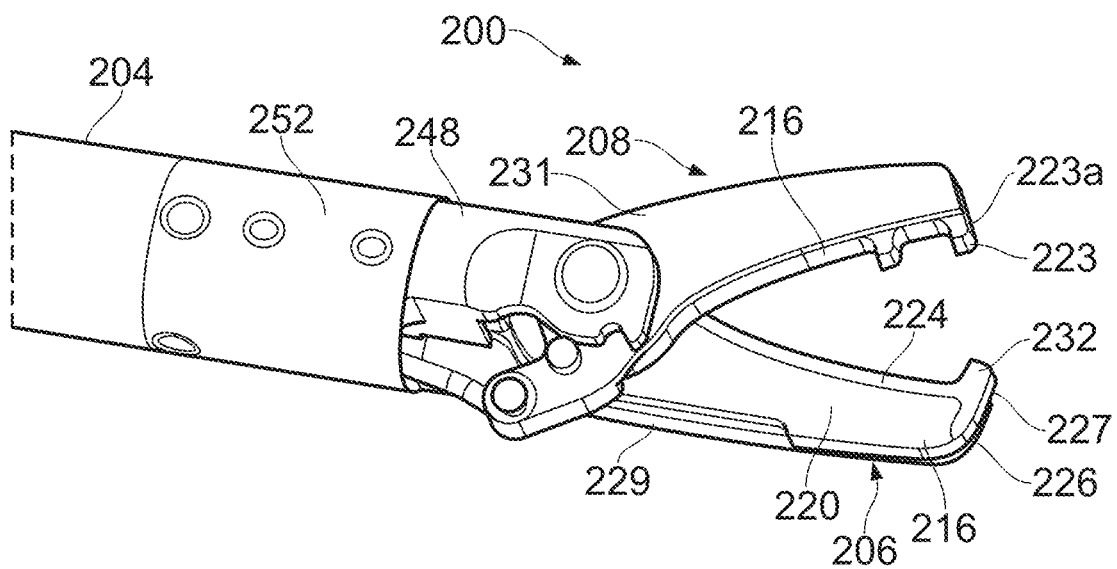
FIG. 3 is another perspective view of the electrosurgical resector tool of FIG. 2 in an intermediate position and including an actuation wire.
Figure 4:
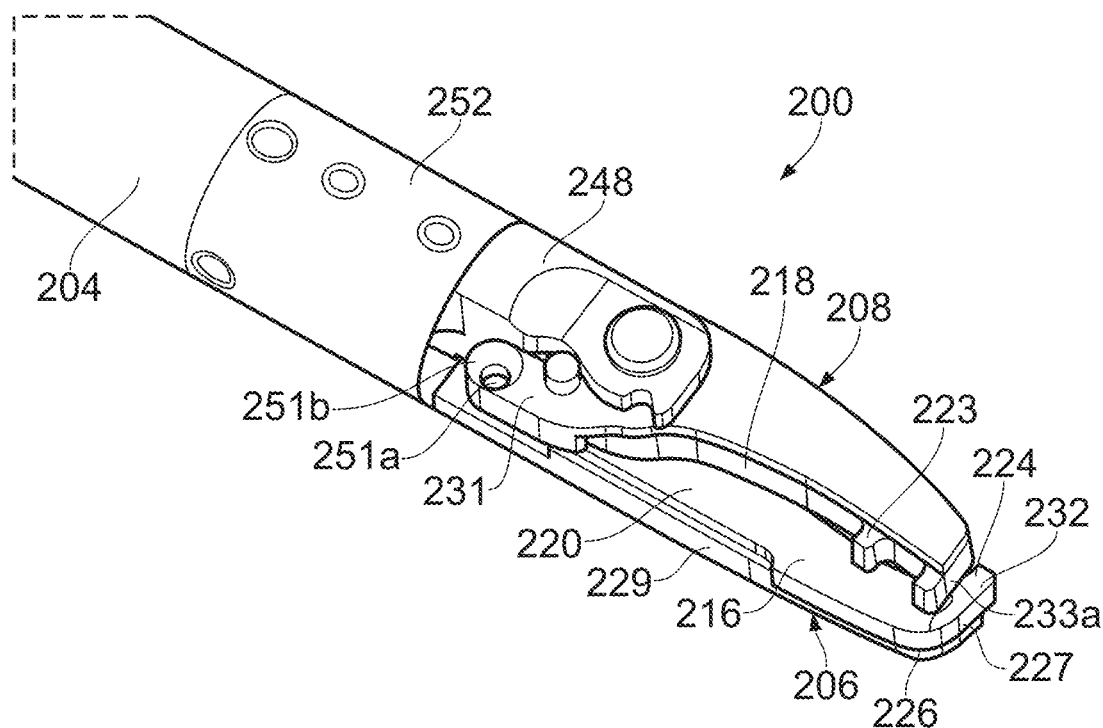
FIG. 4 is a perspective view of the electrosurgical resector tool of FIG. 2 in a closed position.
Figure 5:
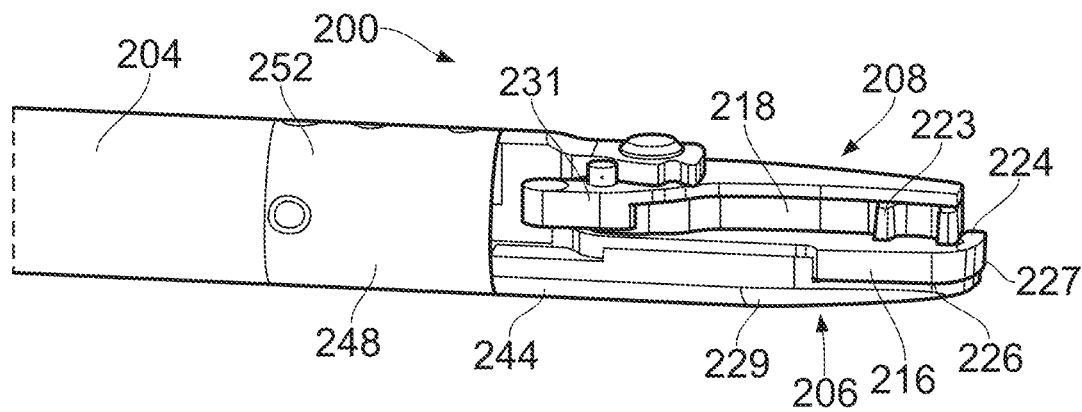
FIG. 5 is another perspective view of the electrosurgical resector tool of FIG. 2 in a closed position.
Figure 6:
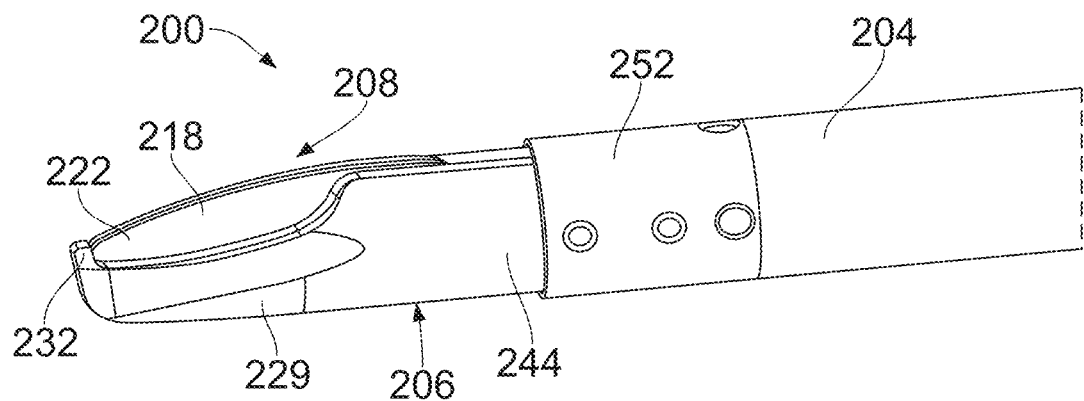
FIG. 6 is another perspective view of the electrosurgical resector tool of FIG. 2 in a closed position.
Figure 7:
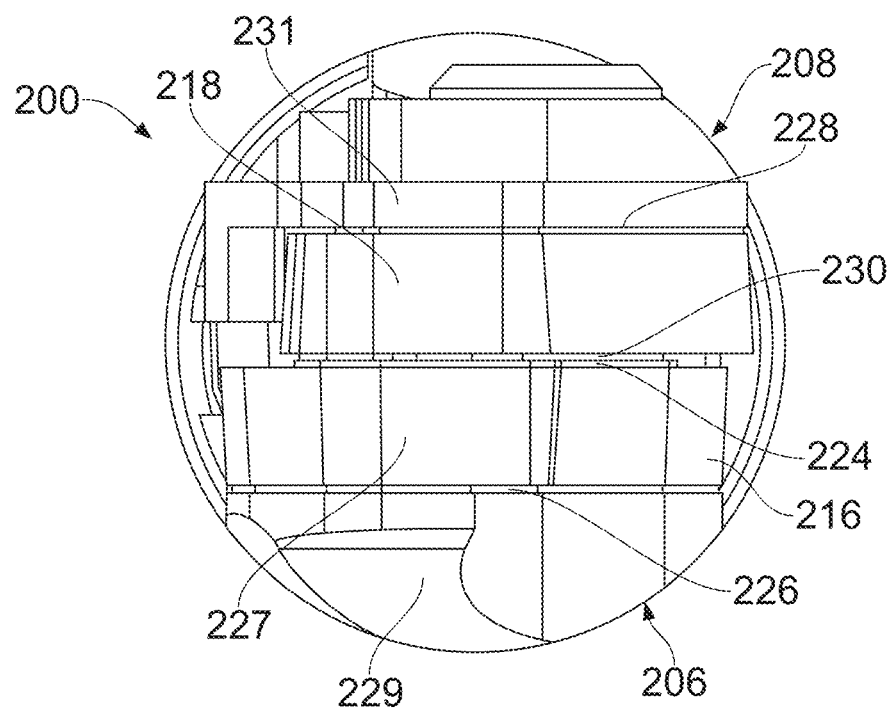
FIG. 7 is a front view onto a distal end face of the electrosurgical resector tool of FIG. 2 in a closed position.

The opening 251a may be a through-hole having an inner diameter and includes a chamfered portion 251b (see FIG. 4). The chamfered portion 251b is adjacent to and in fluid communication with the opening 251a. The chamfered portion 251b has a funnel-shape. The control wire 210 has a rounded distal end (see FIG. 3-FIG. 14 discloses a different embodiment). The distal end of the control wire 210 can be rounded by laser welding. The rounded distal end of the control wire 210 has an outer diameter that is larger than the inner diameter of the opening 251a. Thus, the distal end of the control wire 210 is attached to the opening 251a. A part of the rounded distal end of the control wire 210 is received in the chamfered portion 251b such that only a part of the rounded distal end of the control wire 210 protrudes from the chamfered portion 251b. This and the rounded end reduce the risk that the distal end of the control wire 210 gets hooked with tissue.

The inner electrode 224 of the first jaw 206 and the inner electrode 230 of the first jaw 208 are electrically connected to the inner conductor 234 of the coaxial cable 202. As shown in FIGS. 10 and 12, the first planar dielectric element 216 includes the connecting portion 256 which extends between the first blade element 212 and the distal end of the coaxial cable 202. A distal end of the inner conductor 234 protrudes beyond the distal end of the coaxial cable 202 such that it lies on the connecting portion 256 of the first planar dielectric element 216.

In FIGS. 10 and 12, the first jaw 206 is shown with the inner electrode 224 exposed, for clarity. However, in some embodiments, to ensure that when the jaws 206, 208 are closed there is no electrical connection between the inner electrode 224 of the first jaw and the inner electrode 230 of the second jaw 208, a dielectric coating 225 is applied to the inner surface of the first jaw 206 and of the inner electrode 224. The dielectric coating material 225 may be arranged such that the inner electrode 224 is exposed along the top face of the first jaw 206 to ensure that RF and/or microwave energy may be emitted therefrom, as shown in FIG. 13.

To assemble the tool tip 200, the first base part 244 and first jaw 208 may first be assembled and connected to the distal end of the coaxial cable 202 as shown in FIG. 12. As shown in FIGS. 13, the second jaw 208 is connected to the second base part 248 via the rivet 254. Then, the dielectric block 264 may be glued to the inner surface 220 of the first planar dielectric element 216 (as shown in FIG. 13), following which second base part 248 is mounted on the first base part 244. A dielectric potting material or the adhesive may then be injected into the cavity 235 between the first base part 244 and the second base part 248. The cavity 235 may not be filled with a material. The conductive ring 252 may then be slid over the coaxial cable 202 and onto the first and second mounting portions 246, 250, to hold the first and second base parts 244, 248 together. As noted above, the adhesive may be used to secure the conductive ring 252 over the first and second mounting portions 246, 250. The control wire 210 may then be threaded through the opening 251a in the cover 231, and fixed to the opening 251a on the second jaw 208 (as shown in FIGS. 3 and 14). To this end, the distal end of the control wire 210 can be rounded. Finally, the flexible shaft 204 may be pulled over the coaxial cable 202, and secured to the conductive ring 252, e.g. using an adhesive.

In the embodiment described with reference to FIGS. 2-14, only one of the jaws is movable. However, in other embodiments, both jaws may be movably mounted to the distal end of the coaxial cable 202, e.g. to provide a scissor-like opening and closing of the jaws. It should also be noted that different electrical connections to the electrodes may be used in different embodiments. For instance, in some embodiments, the inner electrode 224 of the first jaw 206 and the inner electrode 230 of the second jaw 208 could be connected to the outer conductor 236, whilst the outer electrode 228 of the second jaw 208 and the outer electrode 226 of the first jaw 206 could be connected to the inner conductor. Various electrode configurations are discussed below with reference to FIGS. 17 to 21.

Figure 15:
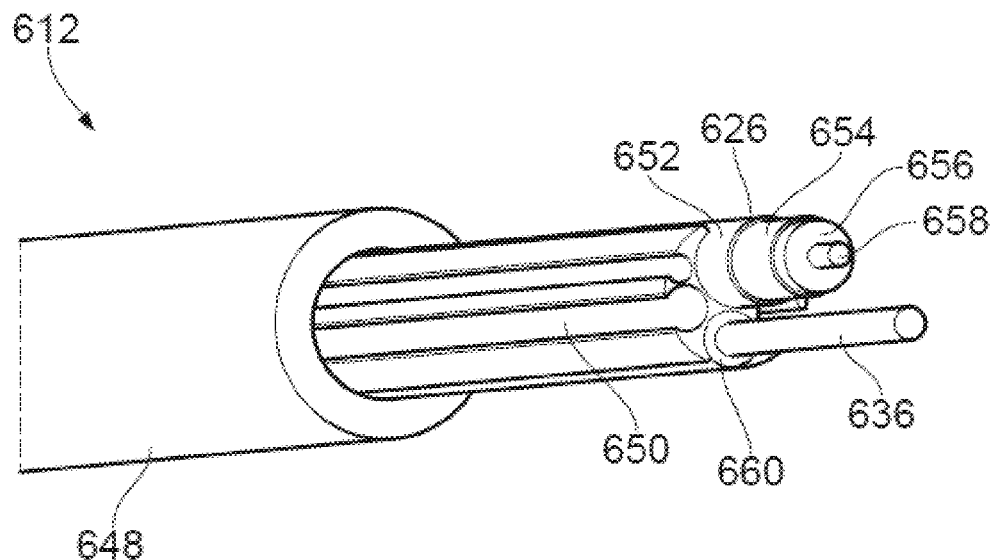
FIG. 15 is a perspective view of the contents of an instrument shaft that can be used with an electrosurgical apparatus that is an embodiment of the invention.
Figure 16:
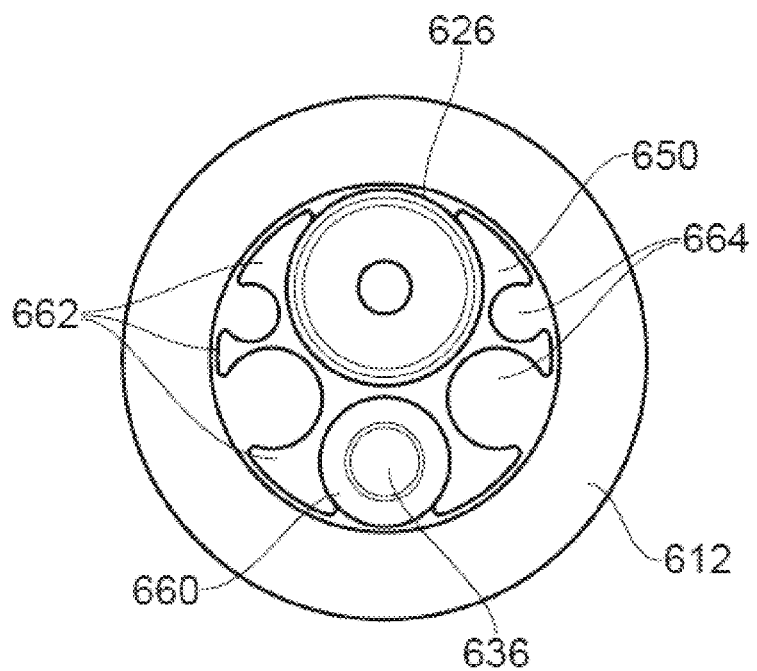
FIG. 16 is a cross-section of the instrument shaft shown in FIG. 16.

FIG. 15 is a cut-away perspective view of the instrument shaft 612 as it travels towards the tool tip. The instrument shaft 612 comprises an outer sleeve 648 that defines a lumen for conveying the coaxial cable 626 and control rod 636. In this example, the coaxial cable 626 and control rod 636 are retained in a longitudinally extending insert 650. The insert 650 is an extrusion, e.g. formed from a deformable polymer such as PEEK or other plastic with similar mechanical properties. As shown more clearly in FIG. 16, the insert 650 is a cylindrical element having a series of sub-lumens 664 cut away around its outer surface. The sub-lumens 664 break through the outer surface of the insert 650 to define a plurality of discrete feet 662 around the circumference thereof. The sub-lumens 664 can be sized to convey components such as the coaxial cable 626 or control rod 636, or may be for the purpose of allowing fluid flow along the lumen of the sleeve 648.

It may be beneficial for the insert not to include any enclosed sub-lumens. Fully enclosed sub-lumens can be prone to retaining deformations if stored in a bent condition. Such deformations can lead to jerky motion in use.

The insert 650 may comprise a sub-lumen for receiving the coaxial cable 626. In this example, the coaxial cable 626 comprises an inner conductor 658 separated from an outer conductor 654 by a dielectric material 656. The outer conductor 654 may in turn have a protective cover or sheath 652, e.g. formed from PTFE or other suitably low friction material to permit relative longitudinal movement between the insert and coaxial cable as the shaft with flexing of the shaft.

Another sub-lumen may be arranged to receive a standard PFTE tube 660 through which the control rod 636 extends. In an alternative embodiment, the control rod 636 may be provided with a low-friction (e.g. PFTE) coating before use, so that a separate PFTE tube is not required.

The insert is arranged to fill, i.e. fit snugly within, the lumen of the sleeve 648 when mounted with the coaxial cable 626 and control rod 636. This means that the insert functions to restrict relative movement between the coaxial cable, control rod and sleeve during bending and rotation of the shaft 612. Moreover, by filling the sleeve 648, the insert helps to prevent the sleeve from collapsing and losing rotation if rotated excessively. The insert is preferably made from a material that exhibits rigidity to resist such movement.

The presence of the insert may furthermore prevent "lost" travel of the control rod caused by deformation of the instrument shaft 612.

The extruded insert discussed above provides cam-like feet that jam on the inside of the sleeve and impede the wrapping of the control rod around the axis of the sleeve. This will reduce the lost travel discussed above.

FIGS. 17 to 21 are schematic diagrams illustrating possible electrode configurations in an electrosurgical resector tool according to embodiments of the invention.

Figure 17:
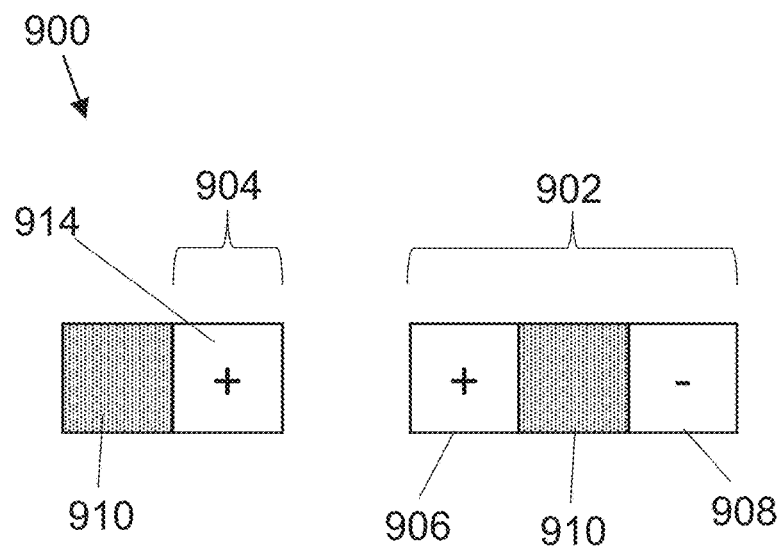
FIG. 17 is a schematic diagram illustrating an tool tip of an electrosurgical resector tool according to an embodiment of the invention.

FIG. 17 shows a schematic cross-sectional diagram of part of an tool tip 900 of an electrosurgical resector tool, having a first jaw 902 and a second jaw 904. The first and second jaws 902, 904 are movable (e.g. pivotable) relative to one another, and each jaw includes a respective blade element for cutting tissue located between the jaws. In a preferred embodiment of the invention, the first jaw 902 may be a static jaw, and the second jaw 904 may be a movable jaw, such as discussed above with respect to FIG. 2. The first jaw 902 includes an inner electrode 906 and an outer electrode 908 which are separated by a dielectric material element 910. The inner electrode 906 is electrically connected to an inner conductor of a coaxial cable of the electrosurgical resector tool, while the outer electrode 908 is electrically connected to an outer conductor of the coaxial cable. The second jaw 904 comprises a single electrode 914, which is also electrically connected to an outer conductor of the coaxial cable. The single electrode 914 may be formed as either an inner electrode or as an outer electrode and may be provided in a similar manner as the inner or outer electrode of the first jaw i.e. attached to a dielectric material element 910. In the schematic diagrams shown by FIGS. 17 to 19, the single electrode 914 is considered as an inner electrode of the second jaw 904, though it should be understood that the description of the connections and emitted fields is substantially the same whether the single electrode is an inner electrode or an outer electrode. The '+' and '-' signs in FIGS. 17 to 19 indicate which of the inner and outer conductors of the coaxial cable each electrode is connected to, with '+' indicating that the electrode is connected to the inner conductor and '-' indicating that the electrode is connected to the outer conductor.

In order to prevent an electrical connection between the inner electrode 906 of the first jaw 902 and the inner electrode 914 of the second jaw 904, the first jaw 902 comprises a second dielectric material element 912 which is positioned on the inner face of the inner electrode 906. The second dielectric material element 912 may be made of the same dielectric material as the first dielectric material element 910 and may, for example, be in the form of a planar dielectric element which is mounted on the first jaw 902. Additionally or alternatively, a piece of dielectric material may be provided on the second jaw 904, such that it covers the inner face of the inner electrode 914 and is located between the inner electrode 906 and the inner electrode 912. Covering each of the inner electrodes with a dielectric material may be preferable to ensure minimal risk of electrical breakdown between the two inner electrodes. This may also improve symmetry between the jaws, which may in turn improve a symmetry of the RF and microwave energy emitted by the tool tip.

Figure 18:
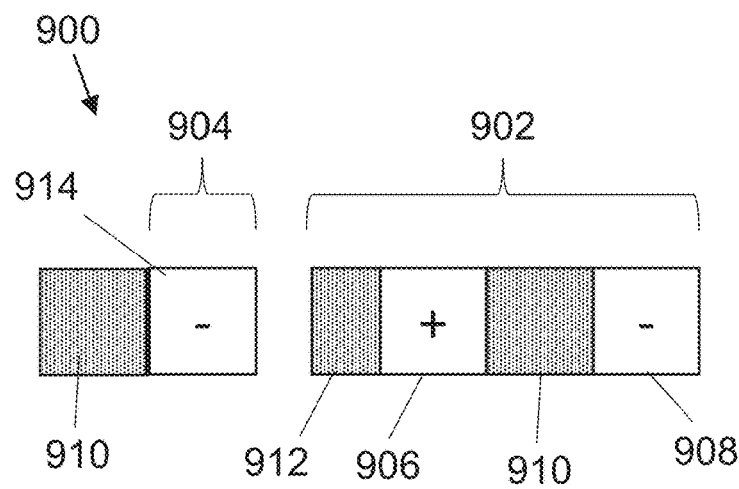
FIG. 18 is a schematic diagram illustrating an tool tip of an electrosurgical resector tool according to a further embodiment of the invention.
Figure 19:
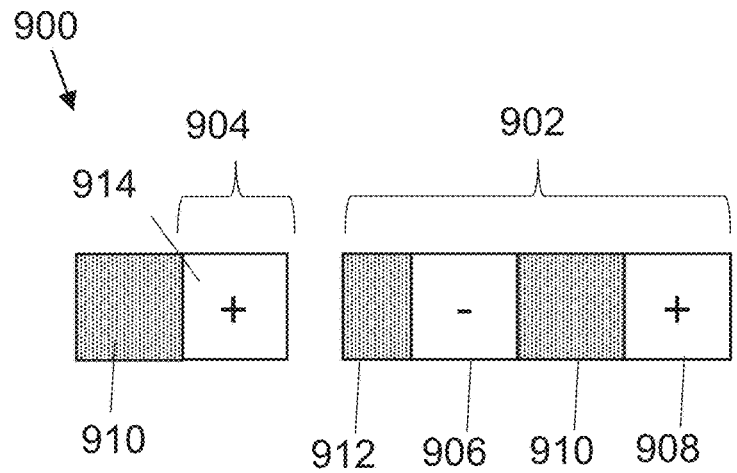
FIG. 19 is a schematic diagram illustrating an tool tip of an electrosurgical resector tool according to a further embodiment of the invention.

With the electrode configuration shown in FIGS. 18 and 19, two RF cutting fields may be generated when RF EM energy is conveyed to the electrodes via the coaxial cable. A first RF cutting field may be established between the inner electrode 906 and the outer electrode 908, both of the first jaw 902, with the inner electrode 906 acting as an active electrode and the outer electrode 908 acting as a first return electrode for the RF EM energy. A second RF cutting field may be established between the inner electrode 906 of the first jaw 902 and the single inner electrode 914 of the second jaw 904, with the inner electrode 906 of the first jaw 902 acting as an active electrode, and the inner electrode 914 of the second jaw 904 acting as a second return electrode for the RF EM energy (or vice versa-see FIG. 19). As a result, the RF cutting fields may be substantially symmetrical about the inner electrode 906 of the first jaw 902, which may enable uniform RF cutting of tissue.

When microwave EM energy is delivered to the electrodes in jaws 902, 904 via the coaxial cable, a microwave field may be established around the jaws. In particular, the electrodes may together act as a microwave field emitting structure (or antenna structure) for emitting the microwave energy. The inner electrode 906 of the first jaw 902 acts as a microwave emitter for emitting the microwave energy. The outer electrode 908 and the inner electrode 914 of the second jaw 904 act as grounded conductors which shape the emitted microwave energy. Such a microwave field emitting structure may result in a substantially symmetrical microwave field being emitted around the jaws.

Figure 20:
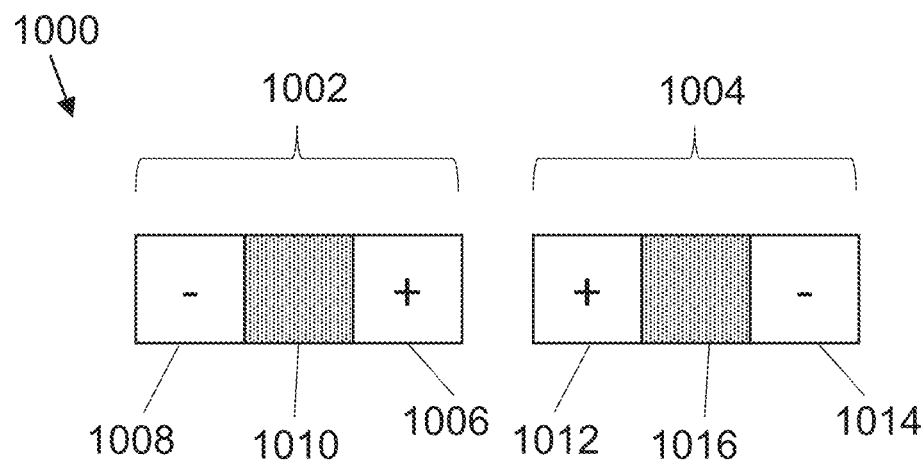
FIG. 20 is a schematic diagram illustrating an tool tip of an electrosurgical resector tool according to a further embodiment of the invention.
Figure 21:
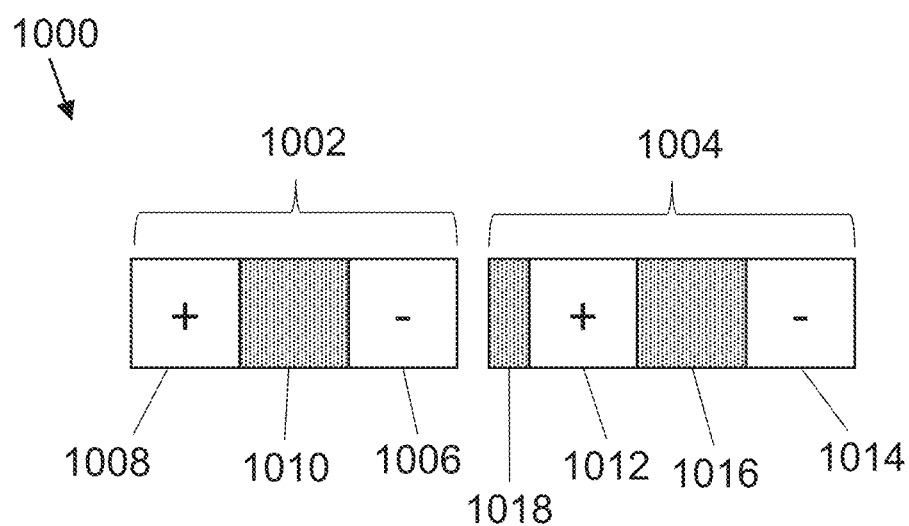
FIG. 21 is a schematic diagram illustrating an tool tip of an electrosurgical resector tool according to a further embodiment of the invention.

FIGS. 20 and 21 show a schematic cross-sectional diagram of part of an tool tip 1000 of an electrosurgical resector tool, having a first jaw 1002 and a second jaw 1004. The first and second jaws are movable (e.g. pivotable) relative to one another, and each jaw includes a respective blade element for cutting tissue located between the jaws. In a preferred embodiment of the invention, the first jaw 1002 may be a static jaw, and the second jaw 1004 may be a movable jaw, such as discussed above with respect to FIG. 2.

In FIG. 20, the first jaw 1002 includes an inner electrode 1006 and an outer electrode 1008 which are separated by a dielectric material element 1010. The inner electrode 1006 is electrically connected to an inner conductor of a coaxial cable of the electrosurgical resector tool, while the outer electrode 1008 is electrically connected to an outer conductor of the coaxial cable. The second jaw 1004 comprises an inner electrode 1012 and an outer electrode 1014 which are separated by a dielectric material element 1016. The inner electrode 1012 is electrically connected to the inner conductor of a coaxial cable of the electrosurgical resector tool, while the outer electrode 1016 is electrically connected to the outer conductor of the coaxial cable. The inner electrodes 1006 and 1012 can contact each other as described in conjunction with FIGS. 10 and 12.

In FIG. 21, the inner electrode 1006 is electrically connected to the outer conductor of a coaxial cable of the electrosurgical resector tool, while the outer electrode 1008 is electrically connected to the outer conductor of the coaxial cable. The inner electrode 1012 of the second jaw 1004 is electrically connected to the inner conductor of the coaxial cable of the electrosurgical resector tool, while the outer electrode 1016 of the second jaw 1004 is electrically connected to the outer conductor of the coaxial cable. In order to prevent an electrical connection between the inner electrode 1006 of the first jaw 1002 and the inner electrode 1012 of the second jaw 1004, the second jaw 1004 comprises a second dielectric material element 1018 which is positioned on the inner face of the inner electrode 1012. The second dielectric material element 1012 may be made of the same dielectric material as the second dielectric material element 1016 and may, for example, be in the form of a planar dielectric element which is mounted on the first jaw 1002. Additionally or alternatively, a piece of dielectric material may be provided on the first jaw 1002, such that it covers the inner face of the inner electrode 1006 and is located between the inner electrode 1006 and the inner electrode 1012. Covering each of the inner electrodes with a dielectric material may be preferable to ensure minimal risk of electrical breakdown between the two inner electrodes. This may also improve symmetry between the jaws, which may in turn improve a symmetry of the RF and microwave energy emitted by the tool tip.

With the electrode configuration shown in FIGS. 20 and 21, two RF cutting fields may be generated when RF EM energy is conveyed to the electrodes via the coaxial cable. A first RF cutting field may be established between the inner electrode 1006 and the outer electrode 1008, both of the first jaw 1002, with the outer electrode 1008 acting as a first active electrode and the inner electrode 1006 active as a return electrode for the RF EM energy. With the embodiment of FIG. 21, a second RF cutting field may be established between the inner electrode 1006 of the first jaw 1002 and the inner electrode 1012 of the second jaw 1004, with the inner electrode 1012 of the second jaw 1004 acting as a second active electrode, and the inner electrode 1006 of the first jaw 1002 acting as a return electrode to the RF EM energy. As a result, the RF cutting fields may be substantially symmetrical about the inner electrode 1006 of the first jaw 1002, which may enable uniform RF cutting of tissue.

When microwave EM energy is delivered to the electrodes in jaws 1002, 1004 via the coaxial cable, a microwave field may be established around the jaws. In particular, the electrodes may together act as a microwave field emitting structure (or antenna structure) for emitting the microwave energy. The inner electrode 1014 of the second jaw 1004 and the outer electrode 1008 of the first jaw 1002 act as microwave emitters for emitter the microwave energy. The inner electrode 1006 of the first jaw 1002 acts as a ground conductor which shapes the emitted microwave energy. Such a microwave field emitting structure may result in a substantially symmetrical microwave field being emitted around the jaws.

Figure 22:
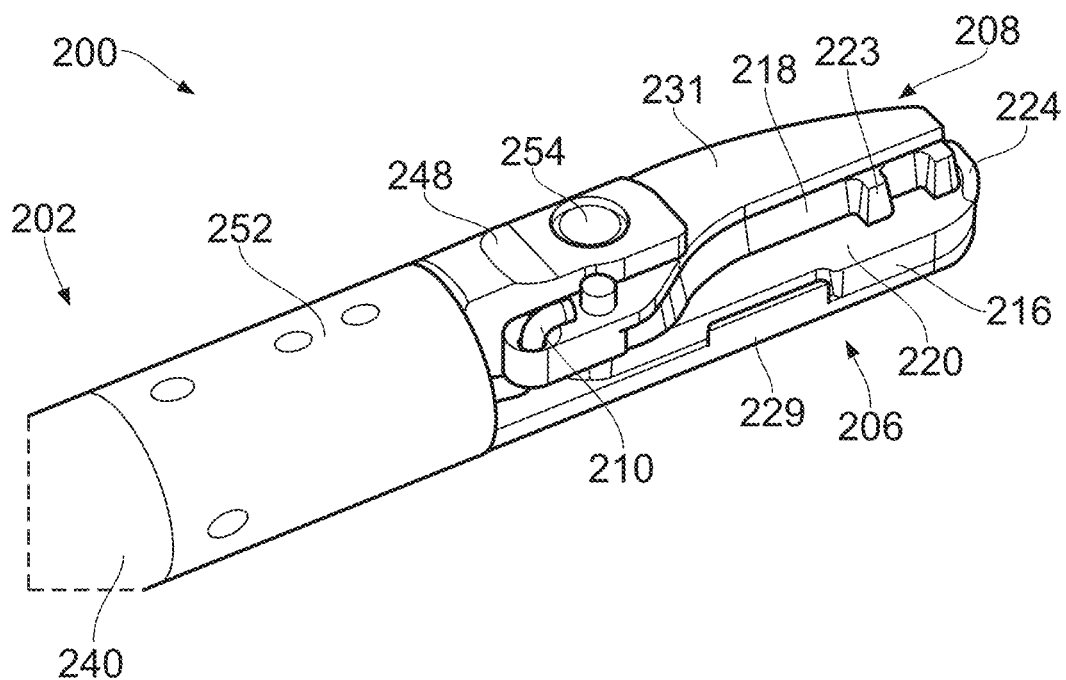
FIG. 22 is a perspective view of an tool tip of an electrosurgical resector tool according to an embodiment of the invention in a closed position.
Figure 23:
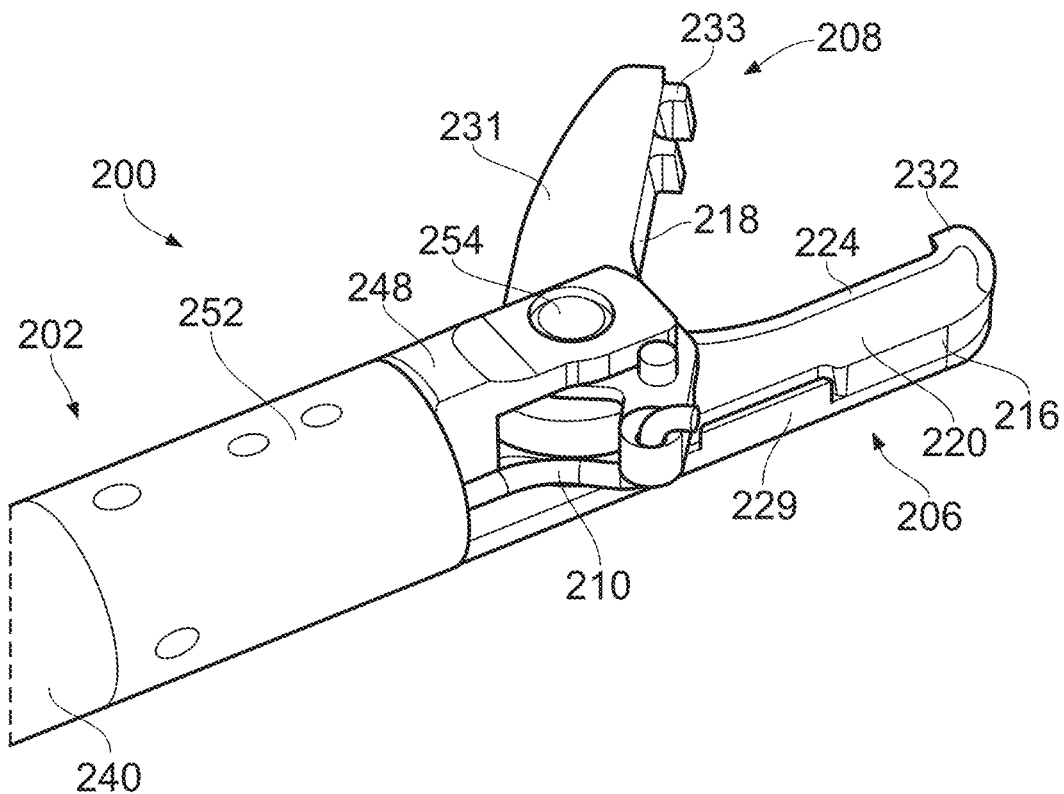
FIG. 23 is another perspective view of the electrosurgical resector tool of FIG. 22 in an intermediate position.

FIGS. 22 and 23 describe a further embodiment of an tool tip 200 of an electrosurgical resector tool. The embodiment of FIGS. 22 and 23 has the same features as the embodiments of FIGS. 1 to 14 except for the following differences: The control wire 210 does not include a rounded distal end. Instead, the control wire 210 is bent above the opening 251a, i.e. between the end of the control wire 210 and the opening 251a. This bending may be considered a second bending. A first bending is the bending between a section of the control wire 210 that extends in the opening 251a and the extension of the control wire 210 along the shaft 204. The first bending and/or the second bending may be 90° bendings. The bent control wire 210 may have an S-shape in a side view. The end of the control wire 210 may be positioned in contact or above the second cover 231. The end of the control wire 210 may not be positioned on a side surface of the second cover 231.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The invention claimed is:

1. An electrosurgical resector tool comprising:
    an energy conveying structure for carrying radiofrequency electromagnetic energy and/or microwave electromagnetic energy;
    a tool tip mounted at a distal end of the energy conveying structure, wherein the tool tip comprises a first jaw and a second jaw;
    wherein the first jaw comprises a first pair of electrodes that are electrically isolated from one another;
    wherein the first pair of electrodes is coupled to the energy conveying structure,
    wherein the first jaw and the second jaw are movable relative to each other between a closed position in which the first jaw and the second jaw lie alongside each other, and an open position in which the second jaw is spaced from the first jaw by a gap for receiving biological tissue;
    wherein the first jaw extends in a distal direction beyond the second jaw in the closed position; and
    wherein the first jaw includes a distal end face,
    wherein the distal end face is arranged such that, in the closed position, when the electrosurgical resector tool is moved in the distal direction, the distal end face firstly comes in contact with the tissue,
    wherein the first jaw includes a first tooth that projects towards the second jaw, the first tooth providing a part of the distal end face such that, in the closed position, when the electrosurgical resector tool is moved in the distal direction, the first tooth firstly comes in contact with the tissue, and wherein the first pair of electrodes is arranged on the first tooth such that the first pair of electrodes is exposed on part of the distal end face that is provided by the first tooth.

2. An electrosurgical resector tool according to claim 1, wherein:
    the first jaw comprises a first planar dielectric element having an inner surface that faces towards the second jaw in the closed position and an outer surface that faces away from the second jaw in the closed position, the first pair of electrodes comprising an inner electrode and an outer electrode, the inner electrode being arranged on the inner surface of the first planar dielectric element and the outer electrode being arranged on the outer surface of the first planar dielectric element; and/or
    the second jaw comprises a second planar dielectric element having an inner surface that faces towards the first jaw in the closed position and an outer surface that faces away from the first jaw in the closed position, and the second jaw comprises:
an inner electrode arranged on the inner surface of the second planar dielectric element, and/or
an outer electrode arranged on the outer surface of the second planar dielectric element.

3. An electrosurgical resector tool according to claim 2, wherein:
the inner electrode of the first jaw comprises a first conductive layer formed on the inner surface of the first planar dielectric element; and/or
the outer electrode of the first jaw comprises a second conductive layer formed on the outer surface of the first planar dielectric element; and/or
the inner electrode of the second jaw comprises a first conductive layer formed on the inner surface of the second planar dielectric element; and/or
the outer electrode of the second jaw comprises a second conductive layer formed on the outer surface of the second planar dielectric element.

4. An electrosurgical resector tool according to claim 2, wherein:
the energy conveying structure comprises a coaxial transmission line having an inner conductor separated from an outer conductor by a dielectric material;
the planar dielectric element of a static jaw of the first jaw and the second jaw extends to the distal end of the energy conveying structure,
the tool tip further comprises
a connection element connecting the inner conductor of the energy conveying structure to the inner electrode of the first pair of electrodes and
a dielectric block arranged between the movable jaw of the first jaw and the second jaw and the distal end of the energy conveying structure,
the connection element is sandwiched between the planar dielectric element of the static jaw and the dielectric block, and
the dielectric block is attached to the planar dielectric element of the static jaw using an adhesive including an adhesive component and particles immersed in the adhesive component.

5. An electrosurgical resector tool according to claim 4, wherein:
a cavity is provided between the dielectric block and the distal end of the energy conveying structure, and
the cavity is filled with the adhesive.

6. An electrosurgical resector tool according to claim 1, wherein:
the first jaw includes a front side facing the second jaw and a rear side facing away from the second jaw,
the first pair of electrodes extends on the distal end face to the front side, and
the first pair of electrodes is spaced from the rear side on the distal end face.

7. An electrosurgical resector tool according to claim 1, wherein:
the second jaw includes at least one second tooth that projects towards the first jaw,
the second tooth includes a front surface facing the distal end face and a back surface facing away from the distal end face, and
in the closed position, the front surface and/or the back surface is distally tilted.

8. An electrosurgical resector tool according to claim 1, further comprising a control wire for actuating a movable jaw of the first jaw and the second jaw,
wherein the movable jaw includes an opening through which the control wire extends for engagement with the movable jaw,
wherein an end of the control wire is rounded and/or
wherein the control wire is bent.

9. An electrosurgical resector tool according to claim 8, wherein:
the rounded end of the control wire has a diameter that is larger than an inner diameter of the opening.

10. An electrosurgical resector tool according to claim 9, wherein:
the movable jaw includes a chamfered portion adjacent to the opening, and
the rounded end of the control wire is at least partially arranged within the chamfered portion.

11. An electrosurgical apparatus comprising:
an electrosurgical generator for supplying radiofrequency electromagnetic energy and/or microwave electromagnetic energy;
a surgical scoping device having an instrument cord for insertion into a patient's body, the instrument cord having an instrument channel extending therethrough; and
an electrosurgical resector tool according to claim 1 inserted through the instrument channel of the surgical scoping device.

* * * * *